United States Patent
Donati et al.

(10) Patent No.: US 11,795,515 B2
(45) Date of Patent: *Oct. 24, 2023

(54) METHODS AND REAGENTS FOR THE SPECIFIC AND SENSITIVE DETECTION OF SARS-COV-2

(71) Applicant: INSTITUT PASTER, Paris (FR)

(72) Inventors: Flora Donati, Paris (FR); Mélanie Albert, Paris (FR); Sylvie Behillil, Paris (FR); Vincent Enouf, Paris (FR); Sylvie van der Werf, Paris (FR)

(73) Assignee: INSTITUT PASTEUR, Paris (FR)

( * ) Notice: Subject to any disclaimer, the term of this patent is extended or adjusted under 35 U.S.C. 154(b) by 302 days.

This patent is subject to a terminal disclaimer.

(21) Appl. No.: 17/210,637

(22) Filed: Mar. 24, 2021

(65) Prior Publication Data

US 2021/0277489 A1 Sep. 9, 2021

Related U.S. Application Data

(62) Division of application No. 16/809,717, filed on Mar. 5, 2020, now Pat. No. 11,001,901.

(51) Int. Cl.
*C12Q 1/68* (2018.01)
*C12Q 1/70* (2006.01)
*C12N 15/10* (2006.01)

(52) U.S. Cl.
CPC .......... *C12Q 1/701* (2013.01); *C12N 15/1096* (2013.01)

(58) Field of Classification Search
CPC ....................................................... C12Q 1/68

USPC ....................................................... 435/6.12
See application file for complete search history.

(56) References Cited

PUBLICATIONS

Corman et al, Detection of 2019 novel coronavirus (2019-nCoV) by real-time RT-PCR, Euro Surveill. Jan. 23, 2020; 25(3): 2000045.*
Chan et al, Improved Molecular Diagnosis of COVID-19 by the Novel, Highly Sensitive and Specific COVID-19-RdRp/Hel Real-Time Reverse Transcription-PCR Assay Validated In Vitro and with Clinical Specimens, J Clin Microbiol. Apr. 23, 2020;58(5):e00310-20. doi: 10.1128/JCM.00310-20, published online Mar. 3, 2020.*
NCBI Accession No. MN975262 (Feb. 11, 2020).*
International Searching Authority in International Application No. PCT/EP2020/055939, dated Nov. 19, 2020.
Who Team: "Molecular assays to diagnose COVID-19: Summary table of available protocols", Jan. 24, 2020 (Jan. 24, 2020), XP055732018, Retrieved from the Internet: URL:https://www.who.int/docs/default-source/coronaviruse/whoinhouseassays.pdf?sfvrsn=de3a76aa 2&download=true [retrieved on Sep. 18, 2020].
Victor M Corman et al: "Detection of 2019 novel coronavirus (2019-nCoV) by real-time RT-PCR", Eurosurveillance, vol. 25, No. 3, Jan. 23, 2020 (Jan. 23, 2020), XP055695049.

* cited by examiner

*Primary Examiner* — Aaron A Priest
(74) *Attorney, Agent, or Firm* — Arrigo, Lee, Guttman & Mouta-Bellum LLP

(57) ABSTRACT

Methods, primers, sets of primers, probes, compositions, and kits for detecting presence or absence of SARS-CoV-2 in a sample are provided.

10 Claims, No Drawings

Specification includes a Sequence Listing.

METHODS AND REAGENTS FOR THE SPECIFIC AND SENSITIVE DETECTION OF SARS-COV-2

FIELD OF THE INVENTION

The invention relates to methods and reagents to detect the presence and/or absence of the 2019 novel coronavirus (SARS-CoV-2, 2019-nCov or COVID-19) in a sample. The methods and reagents are useful for screening samples for presence and/or absence of SARS-CoV-2 and may therefore be used to screen subjects to identify individuals infected with SARS-CoV-2, among other uses.

BACKGROUND OF THE INVENTION

In December 2019, patients presenting with viral pneumonia were reported in Wuhan, China. A novel coronavirus was subsequently identified as the causative agent, and provisionally named 2019 novel coronavirus (2019-nCov or SARS-CoV-2) (Zhu N et al., N Engl J Med., 2020 Jan. 24). The virus swiftly spread within and outside China, leading to the WHO declaring a Public Health Emergency of International Concern on Jan. 30, 2020. With the aim of rapid development of an assay for detection of the presence and/or absence of SARS-CoV-2 in a sample, and based on state of the art real-time RT-PCR technology, two targets in the RNA-dependent RNA polymerase (RdRP) gene of the virus were identified herein by the inventors.

Coronaviruses are enveloped, positive single stranded RNA viruses. Coronaviruses have been identified in various mammalians hosts such as bats, camels, or mice, among others. Several coronaviruses are pathogenic to humans, leading to varying severity of symptoms (Cui et al., Nat Rev Microbiol. 2019 March; 17(3):181-92). Highly pathogenic variants include the severe acute respiratory syndrome coronavirus (SARS-Cov) that emerged in China in 2002, resulting in ~8000 human infections and 700+ deaths (Peiris et al., Nat Med., 2004 December; 10(12 Suppl):S88-97) and the Middle East respiratory syndrome coronavirus (MERS-CoV), first detected in Saudi Arabia in 2012 and responsible for ~2500 human infections and 850+ deaths (Zaki et al., N Engl J Med., 2012 Nov. 8; 367(19):1814-20; Lee et al., BMC Infect Dis. 2017 Jul. 14; 17(1):498).

Coronavirus genomes encodes non-structural polyprotein and structural proteins, including the Spike (S), envelope, membrane and nucleocapsid proteins. The coronavirus RNA genome has a 5' methylated cap and a 3' polyadenylated tail, which allows the RNA to attach to the host cell's ribosome for translation. Coronavirus genomes encode a protein called RNA-dependent RNA polymerase (RdRp), which allows the viral genome to be transcribed into new RNA copies using the host cell's machinery. The RdRp is the first protein to be made; once the gene encoding the RdRp is translated, translation is stopped by a stop codon. RNA-dependent RNA polymerase (RdRp, RDR) is an enzyme that catalyzes the replication of RNA from an RNA template. This is in contrast to a typical DNA-dependent RNA polymerase, which catalyzes the transcription of RNA from a DNA template. RdRP is an essential protein encoded in the genomes of all RNA-containing viruses with no DNA stage. It catalyzes synthesis of the RNA strand complementary to a given RNA template. The RNA replication process is a two-step mechanism. First, the initiation step of RNA synthesis begins at or near the 3' end of the RNA template by means of a primer-independent (de novo), or a primer-dependent mechanism that utilizes a viral protein genome-linked (VPg) primer. The de novo initiation consists in the addition of a nucleoside triphosphate (NTP) to the 3'-OH of the first initiating NTP. During the following so-called elongation phase, this nucleotidyl transfer reaction is repeated with subsequent NTPs to generate the complementary RNA product.

There is an urgent need for new methods and reagents to identify with specificity and improved sensitivity the presence and/or absence of SARS-CoV-2 in samples. This invention as depicted hereinafter was designed and tested by the National Reference Center for Respiratory Virus, Institut Pasteur Paris, in panels of patients in France suspected to be infected by SARS-CoV-2 or in close contact with individuals known to be infected by SARS-CoV-2. Following the results, this PCR test showed 100% positive detection of about at least as low as 100 copies of target RNA per reaction in singleplex or 10 copies in multiplex using the selected 2 pairs of primers described below. This test is not reactive to other coronavirus, nor to other viruses causing respiratory infections, and distress in some patients. This test which is now validated on a panel of SARS-CoV-2 of 600 positive and negative patients, including asymptomatic contact individuals, individuals returning from epidemic zone, and symptomatic patients. Within symptomatic patients, as there is also a concurrent epidemic of flu in France, negative patients with the SARS-CoV2 test of the invention were confirmed to be infected by flu or other respiratory diseases. The validation of this test will now allow dispatch for diagnosis to reference hospitals in France and abroad, and within the international network of Institut Pasteur around the world.

SUMMARY OF THE INVENTION

The inventors have designed methods and reagents comprising novel nucleic acids that may be used as primers and/or probes, and are based in part on the inventors' discovery that these nucleic acids enable detection of the presence and/or absence of SARS-CoV-2 with very desirable sensitivity and specificity.

In a first aspect the invention provides a first method for detecting the presence or absence of a SARS-CoV-2 RNA in a sample, comprising: providing a sample; subjecting the sample to a reverse transcription reaction with a SARS-CoV-2-specific reverse primer to generate specific cDNA copy of SARS-CoV-2 RNA in the sample, wherein the reverse primer hybridizes to the sequence: 5'-ACAACACAACAAAGGGAG-3' (SEQ ID NO:11) and the RNA equivalent thereof; amplifying any resultant cDNA; and detecting any amplified product with a probe that hybridizes to the sequence: 5'-TACCGGCAGCACAA-GACATCT-3' (SEQ ID NO:12) or the complement thereof. In some embodiments, the resultant cDNA is amplified with the reverse primer and a forward primer, wherein the forward primer hybridizes to the sequence: 5'-CAACAGGACTAAGCTCAT-3' (SEQ ID NO: 10).

In a preferred embodiment of the method, the reverse primer comprises the sequence 5' CTCCCTTTGTTGTGTTGT-3' (SEQ ID NO: 2), or a variant thereof, and is from 15 to 21 bases in length; and/or the forward primer comprises the sequence 5' ATGAGCT-TAGTCCTGTTG-3' (SEQ ID NO: 1), or a variant thereof, and is from 15 to 21 bases in length; and/or the probe comprises the sequence 5' AGATGTCTTGTGCTGCCGGTA 3' (SEQ ID NO: 3), or a variant thereof, or the complement of either of these, and is from 18 to 24 bases in length.

In a more preferred embodiment of the method, the reverse primer consists of the sequence 5' CTCCCTTTGTTGTGTTGT-3' (SEQ ID NO: 2); and/or the forward primer consists of the sequence 5' ATGAGCT-TAGTCCTGTTG-3' (SEQ ID NO: 1); and/or the probe consists of the sequence 5' AGATGTCTTGTGCTGCCGGTA 3' (SEQ ID NO: 3), or the complement thereof.

In a still more preferred embodiment of the method, the reverse primer consists of the sequence 5' CTCCCTTTGTTGTGTTGT-3' (SEQ ID NO: 2); the forward primer consists of the sequence 5' ATGAGCT-TAGTCCTGTTG-3' (SEQ ID NO: 1); and the probe consists of the sequence 5' AGATGTCTTGTGCTGCCGGTA 3' (SEQ ID NO: 3), or the complement thereof.

In another aspect the invention provides a second method for detecting the presence or absence of a SARS-CoV-2 RNA in a sample, comprising: providing a sample; subjecting the sample to a reverse transcription reaction with a specific reverse primer to generate a cDNA copy of SARS-CoV-2 RNA in the sample, wherein the reverse primer hybridizes to the sequence: 5'-CCTATAT-TAACCTTGACCAG-3' (SEQ ID NO:14) and the RNA equivalent thereof; amplifying any resultant cDNA; and detecting any amplified product with a probe that hybridizes to the sequence: 5'-CCTGGCGTGGTTTGTATGA-3' (SEQ ID NO:15) or the complement thereof. In some embodiments, the resultant cDNA is amplified with the reverse primer and a forward primer, wherein the forward primer hybridizes to the sequence: 5'-CGAAATCATACCAGT-TACC-3' (SEQ ID NO:13).

In a preferred embodiment of the second method, the reverse primer comprises the sequence 5' CTGGT-CAAGGTTAATATAGG-3' (SEQ ID NO: 5), or a variant thereof, and is from 17 to 23 bases in length; and/or the forward primer comprises the sequence 5' GGTAACTGGTATGATTTCG-3' (SEQ ID NO: 4), or a variant thereof, and is from 16 to 22 bases in length; and/or the probe comprises the sequence 5' TCATACAAAC-CACGCCAGG 3' (SEQ ID NO: 6), or a variant thereof, or the complement of either of these, and is from 16 to 22 bases in length.

In a more preferred embodiment of the method, the reverse primer consists of the sequence 5' CTGGT-CAAGGTTAATATAGG-3' (SEQ ID NO: 5); and/or the forward primer consists of the sequence 5' GGTAACTGGTATGATTTCG-3' (SEQ ID NO: 4); and/or the probe consists of the sequence 5' TCATACAAAC-CACGCCAGG 3' (SEQ ID NO: 6), or the complement thereof.

In a still more preferred embodiment of the second method, the reverse primer consists of the sequence 5' CTGGTCAAGGTTAATATAGG-3' (SEQ ID NO: 5); the forward primer consists of the sequence 5' GGTAACTGGTATGATTTCG-3' (SEQ ID NO: 4); and the probe consists of the sequence 5' TCATACAAAC-CACGCCAGG 3' (SEQ ID NO: 6), or the complement thereof.

In another aspect the invention provides a third method for detecting the presence or absence of a SARS-CoV-2 RNA in a sample. The third method combines the first and second methods to provide a combinatorial assay.

In another aspect the invention provides a fourth method for detecting the presence or absence of a SARS-CoV-2 RNA in a sample, comprising: providing a sample; subjecting the sample to a reverse transcription reaction with a SARS-CoV-2 specific reverse primer to generate a cDNA copy RNA in the sample; amplifying any resultant DNA with the reverse primer and a SARS-CoV-2 specific forward primer, wherein the reverse and forward primers amplify a target sequence of SARS-CoV-2 RNA selected from the group consisting of the sequences SEQ ID NO: 16 and SEQ ID NO: 17 and the variants thereof comprising the addition of up to 20 consecutive nucleotides of 5' and/or 3' flanking sequence from said SARS-CoV-2 RNA or the deletion of up to 20 consecutive nucleotides at one or both ends of said sequences; and detecting any amplified product with a SARS-CoV-2 specific probe. In some embodiments, the forward and reverse primer and the probe are as described above for the first and second method. In some embodiments, the method combines the amplification of the target sequence SEQ ID NO: 16 or a variant thereof and the target sequence SEQ ID NO: 17 or a variant thereof.

In some embodiments, the method is an RT-PCR method.

In some embodiments, the method comprises reverse transcribing and amplifying an internal positive control. In a preferred embodiment, the internal positive control reverse primer comprises the sequence 5' ATAT-TGCAGCAGTACGCACACA-3' (SEQ ID NO: 8), or a variant thereof, and is from 19 to 25 bases in length; and/or the internal positive control forward primer comprises the sequence 5' ACAGGTACGTTAATAGTTAATAGCGT-3' (SEQ ID NO: 7), or a variant thereof, and is from 23 to 29 bases in length; and/or the internal positive control probe comprises the sequence 5' ACACTAGCCATCCT-TACTGCGCTTCG 3' (SEQ ID NO: 9), or a variant thereof, or the complement of either of these, and is from 23 to 29 bases in length.

In some embodiments of the methods, the probe and the internal positive control probe are labelled with 6-carboxy-fluorescein (6FAM) or hexachloro-6-carboxy-fluorescein (HEX) at the 5' end.

In some embodiments of the methods, the probe and the internal positive control probe are labelled with black hole quencher 1 (BHQ1) at the 3' end.

In some embodiments of the methods, the coronavirus is SARS-CoV-2 and is not other coronavirus, nor other viruses causing respiratory diseases.

In another aspect the invention provides a primer for use in the amplification of a SARS-CoV-2 RNA in a sample, wherein the primer: hybridizes to the sequence: 5'-ACAACACAACAAAGGGAG-3' (SEQ ID NO:11) and the RNA equivalent thereof; hybridizes to the sequence: 5'-CAACAGGACTAAGCTCAT-3' (SEQ ID NO:10); hybridizes to the sequence: 5'-CCTATAT-TAACCTTGACCAG-3' (SEQ ID NO:14) and the RNA equivalent thereof; or hybridizes to the sequence: 5'-CGAAATCATACCAGTTACC-3' (SEQ ID NO:13).

In a preferred embodiment, the primer comprises the sequence 5' CTCCCTTTGTTGTGTTGT-3' (SEQ ID NO: 2), or a variant thereof, and is from 15 to 21 bases in length; comprises the sequence 5' ATGAGCTTAGTCCTGTTG-3' (SEQ ID NO: 1), or a variant thereof, and is from 15 to 21 bases in length; comprises the sequence 5' CTGGT-CAAGGTTAATATAGG-3' (SEQ ID NO: 5), or a variant thereof, and is from 17 to 23 bases in length; or comprises the sequence 5' GGTAACTGGTATGATTTCG-3' (SEQ ID NO: 4), or a variant thereof, and is from 16 to 22 bases in length.

In a more preferred embodiment, the primer consists of the sequence 5' CTCCCTTTGTTGTGTTGT-3' (SEQ ID NO: 2); consists of the sequence 5'-ATGAGCT-TAGTCCTGTTG-3' (SEQ ID NO: 1); consists of the sequence 5'-CTGGTCAAGGTTAATATAGG-3' (SEQ ID NO: 5); or consists of the sequence 5'-GGTAACTGGTAT-GATTTCG-3' (SEQ ID NO: 4).

In another aspect the invention provides a set of primers for use in the amplification of a SARS-CoV-2 RNA in a sample, wherein the primer set comprises: a first primer that hybridizes to the sequence: 5'-ACAACACAACAAAGG-GAG-3' (SEQ ID NO:11) and the RNA equivalent thereof; and a second primer that hybridizes to the sequence: 5'-CAACAGGACTAAGCTCAT-3' (SEQ ID NO:10).

In a preferred embodiment, primer set comprises: a first primer comprising the sequence 5' CTCCCTTTGTTGTGTTGT-3' (SEQ ID NO: 2), or a variant thereof, that is from 15 to 21 bases in length; and a second primer comprising the sequence 5' ATGAGCT-TAGTCCTGTTG-3' (SEQ ID NO: 1), or a variant thereof, that is from 15 to 21 bases in length.

In a more preferred embodiment, the first primer consists of the sequence 5' CTCCCTTTGTTGTGTTGT-3' (SEQ ID NO: 2); and the second primer consists of the sequence 5' ATGAGCTTAGTCCTGTTG-3' (SEQ ID NO: 1).

In another aspect, the invention provides an alternative set of primers, wherein the primer set comprises: a first primer that hybridizes to the sequence: 5'-CCTATAT-TAACCTTGACCAG-3' (SEQ ID NO:14) and the RNA equivalent thereof; and a second primer that hybridizes to the sequence: 5' CGAAATCATACCAGTTACC-3' (SEQ ID NO:13).

In a preferred embodiment, the primer set comprises: a first primer comprising the sequence 5'-CTGGTCAAGGT-TAATATAGG-3' (SEQ ID NO: 5), or a variant thereof, and is from 17 to 23 bases in length; or a second primer comprising the sequence 5' GGTAACTGGTATGATTTCG-3' (SEQ ID NO: 4), or a variant thereof, and is from 16 to 22 bases in length.

In a more preferred embodiment, the first primer consists of the sequence 5'-CTGGTCAAGGTTAATATAGG-3' (SEQ ID NO: 5); and the second primer consists of the sequence 5'-GGTAACTGGTATGATTTCG-3' (SEQ ID NO: 4).

In another aspect, the invention provides an alternative set of primers, for use in the amplification of a SARS-CoV-2 RNA in a sample, wherein the primer set comprises: a first primer that hybridizes to the sequence: 5'-ACAACACAACAAAGGGAG-3' (SEQ ID NO:11) and the RNA equivalent thereof; a second primer that hybridizes to the sequence: 5'-CAACAGGACTAAGCTCAT-3' (SEQ ID NO:10); a third primer that hybridizes to the sequence: 5'-CCTATATTAACCTTGACCAG-3' (SEQ ID NO:14) and the RNA equivalent thereof; and a fourth primer that hybridizes to the sequence: 5' CGAAATCATACCAGTTACC-3' (SEQ ID NO:13).

In a preferred embodiment, the primer set comprises: a first primer comprising the sequence 5' CTCCCTTTGTTGTGTTGT-3' (SEQ ID NO: 2), or a variant thereof, that is from 15 to 21 bases in length; a second primer comprising the sequence 5' ATGAGCT-TAGTCCTGTTG-3' (SEQ ID NO: 1), or a variant thereof, that is from 15 to 21 bases in length; a third primer comprising the sequence 5' CTGGTCAAGGT-TAATATAGG-3' (SEQ ID NO: 5), or a variant thereof, and is from 17 to 23 bases in length; and a fourth primer comprising the sequence 5' GGTAACTGGTATGATTTCG-3' (SEQ ID NO: 4), or a variant thereof, and is from 16 to 22 bases in length.

In a preferred embodiment, the first primer consists of the sequence 5' CTCCCTTTGTTGTGTTGT-3' (SEQ ID NO: 2); the second primer consists of the sequence 5'-AT-GAGCTTAGTCCTGTTG-3' (SEQ ID NO: 1); the third primer consists of the sequence 5'-CTGGTCAAGGT-TAATATAGG-3' (SEQ ID NO: 5); and the fourth primer consists of the sequence 5' GGTAACTGGTATGATTTCG-3' (SEQ ID NO: 4).

In another aspect the invention provides a set of primers for use in in the specific amplification of SARS-CoV-2 RNA in a sample, which comprises a SARS-CoV-2-specific forward primer and reverse primer which amplify the sequence SEQ ID NO: 16 or 17 or a variant thereof comprising the addition of up to 20 consecutive nucleotides of 5' and/or 3' flanking sequence from SARS-CoV-2 RNA or the deletion of up to 20 consecutive nucleotides at one or both ends of said sequences.

In another aspect, the invention provides a probe for use in the detection of amplification products of a SARS-CoV-2 RNA in a sample, wherein the probe hybridizes to the sequence: 5'-TACCGGCAGCACAAGACATCT-3' (SEQ ID NO:12) or the complement thereof; or wherein the probe hybridizes to the sequence: 5'-CCTGGCGTGGTTTGTATGA-3' (SEQ ID NO:15) or the complement thereof.

In a preferred embodiment, the probe comprises the sequence 5' AGATGTCTTGTGCTGCCGGTA 3' (SEQ ID NO: 3), or a variant thereof, or the complement of either of these, and is from 18 to 24 bases in length; or the probe comprises the sequence 5' TCATACAAACCACGCCAGG 3' (SEQ ID NO: 6), or a variant thereof, or the complement of either of these, and is from 16 to 22 bases in length.

In a more preferred embodiment, the probe consists of the sequence 5' AGATGTCTTGTGCTGCCGGTA 3' (SEQ ID NO: 3), or the complement thereof; or the probe consists of the sequence 5' TCATACAAACCACGCCAGG 3' (SEQ ID NO: 6), or the complement thereof.

In some embodiments the probe is labelled with 6-carboxy-fluorescein (6FAM) or hexachloro-6-carboxy-fluorescein (HEX) at the 5' end.

In some embodiments the probe is labelled with black hole quencher 1 (BHQ1) at the 3' end.

Also provided is a composition comprising a set of primers as described herein and a probe as described herein.

Also provided is a kit comprising a set of primers as described herein and a probe as described herein. In some embodiments the kit further comprises an internal negative control. In some embodiments the kit further comprises an internal positive control. In a preferred embodiment, the internal positive control comprises: a reverse primer comprising the sequence 5' ATAT-TGCAGCAGTACGCACACA-3' (SEQ ID NO: 8), or a variant thereof, that is from 19 to 25 bases in length; and/or a forward primer comprising the sequence 5' ACAGGTACGTTAATAGTTAATAGCGT-3' (SEQ ID NO: 7), or a variant thereof, that is from 23 to 29 bases in length; and/or a probe comprising the sequence 5' ACACTAGC-CATCCTTACTGCGCTTCG 3' (SEQ ID NO: 9), or a variant thereof, or the complement of either of these, that is from 23 to 29 bases in length.

In some embodiments the kit further comprises a reverse transcriptase.

In some embodiments the kit further comprises a DNA polymerase.

In some embodiments the kit further comprises dNTPs.

In preferred embodiments of the primer, set of primers, probe, composition, or kit is specific to SARS-CoV-2.

DETAILED DESCRIPTION OF THE INVENTION

As used herein a "variant" of a reference sequence of nucleotides is a modified form in which at least one nucleotide is added, deleted, or substituted. In some embodiments the variant includes only addition of one or more nucleotides. In some embodiments the variant includes only deletion of one or more nucleotides. In some embodiments the variant includes only substitution of one or more nucleotides. In some embodiments the variant includes addition and deletion of different nucleotides. An addition is a change that increases the total number of nucleotides in the sequence while a deletion is a change that decreases the total number of nucleotides. In some embodiments the addition and/or deletion occurs at only one end while in other embodiments it occurs at both ends. In some embodiments an addition or deletion is internal. In some embodiments the variant includes only one nucleotide that is added, deleted, or substituted. In some embodiments 2, 3, 4, 5, 6, 7, 8, 9 or 10 or more nucleotides are added, deleted, or substituted. A variant according to the invention hybridizes to SARS-CoV-2 nucleic acid (RNA, DNA equivalent or complement thereof). In this context, the term "hybridizes to" refers to the ability of the variant to form a double-stranded hybrid molecule with SARS-CoV-2 nucleic acid.

According to standard practice in the field of virology, the sequences of coronavirus genome (positive single stranded RNA) or fragments thereof (target sequences for SARS-CoV-2 RNA amplification) are disclosed in the DNA form. Therefore, the sequence SEQ ID NO: 19 is the DNA equivalent of SARS-CoV-2 RNA and the sequences SEQ ID NO: 16 and SEQ ID NO: 17 are the DNA equivalent of SARS-CoV-2 RNA target sequences for SARS-CoV-2 RNA amplification.

SARS-CoV-2 Nucleic Acid Sequences

Based on the first sequences of SARS-CoV-2 made available on the GISAID database on Jan. 11, 2020 (SEQ ID NO: 19), primers and probes (nCoV_IP2 and nCoV_IP4) were designed to target the RdRp gene spanning nt 12621-12727 and 14010-14116 (positions according SARS-CoV, NC_004718). These positions correspond to nt 12669-12776 and 14059-14165 in SARS-CoV-2 sequence (SEQ ID NO: 19).

The following table lists preferred embodiments of SARS-CoV-2 nucleic acid sequences of this disclosure, which were identified by the inventors as described in the examples. The primer/probe column lists the sequences of the forward primer, reverse primer, and probe used in the Example. The Target Sequence (reverse complement) column lists the reverse complement (i.e., target) of the primer/ probe sequence. The sequences are represented as DNA but in alternative embodiments at least one of the nucleotides may be an RNA nucleotide.

| | Primer/Probe | Target Sequence (reverse complement) |
|---|---|---|
| RdRp gene/nCoV_IP2 | | |
| nCoV_IP2-12669Fw | ATGAGCTTAGTCCTGTTG (SEQ ID NO: 1) | CAACAGGACTAAGCTCAT (SEQ ID NO: 10) |
| nCoV_IP2-12759Rv | CTCCCTTTGTTGTGTTGT (SEQ ID NO: 2) | ACAACACAACAAAGGGAG (SEQ ID NO: 11) |
| nCoV_IP2-12696bProbe(+) | AGATGTCTTGTGCTGCCGGTA (SEQ ID NO: 3) | TACCGGCAGCACAAGACATCT (SEQ ID NO: 12) |
| RdRp gene/nCoV_IP4 | | |
| nCoV_IP4-14059Fw | GGTAACTGGTATGATTTCG (SEQ ID NO: 4) | CGAAATCATACCAGTTACC (SEQ ID NO: 13) |
| nCoV_IP4-14146Rv | CTGGTCAAGGTTAATATAGG (SEQ ID NO: 5) | CCTATATTAACCTTGACCAG (SEQ ID NO: 14) |
| nCoV_IP4-14084Probe(+) | TCATACAAACCACGCCAGG (SEQ ID NO: 6) | CCTGGCGTGGTTTGTATGA (SEQ ID NO: 15) |

Methods for Detection

The invention encompasses methods for specific detection of SARS-CoV-2. In one embodiment, the method comprises providing a sample, subjecting the sample to a reverse transcription reaction to generate a cDNA copy SARS-CoV-2 RNA in the sample using a "reverse primer" specific for coronavirus, amplifying any resultant DNA with the "reverse primer" and a "forward primer," and detecting any amplified product with a "probe." The method can be used for the determination of whether or not SARS-CoV-2 is present in the sample.

In some embodiments, the sample is an environmental sample, such as soil, food, beverages, feed, water (e.g., fresh water, salt water, waste water, and drinking water), sewage, sludge, and surfaces or samples obtained from surface swipes. In preferred embodiments, the sample is a biological sample, for example, stool, saliva, blood, plasma, serum, urine, cerebrospinal fluid, or tissue sample.

The sample can be subjected to well-known isolation and purification protocols or used directly. For example, the sample can be subjected to a treatment to release/extract the nucleic acids of the sample and/or to remove proteins and other non-nucleic acid components of the sample using conventional techniques, such as those in the Examples.

Reverse transcription of the RNA of a coronavirus strain can be performed with a "reverse primer" specific for coronavirus. A "reverse primer" is one that, based on its 5'-3' orientation, can bind to a single-stranded RNA and serve to initiate generation of a complementary DNA (cDNA) copy of the RNA. The reverse transcription can be accomplished using well known and routine methods. The reaction mix for reverse transcription contains the reagents for the reaction, for example, a reverse primer, dNTPs (dATP, dCTP, dGTP and dTTP), a buffer, and a reverse transcriptase. Exemplary reaction conditions are set forth in the examples.

Amplification of the cDNA copy of a coronavirus strain generated by reverse transcription can be performed with a "forward primer" specific for coronavirus. A "forward primer" is one that, based on its 5'-3' orientation, can bind to a single-stranded antisense cDNA copy of an RNA generated by reverse transcription and serve to initiate generation of a double-stranded DNA copy of the RNA. The amplification can be accomplished using well known and routine methods. The reagent mix for amplification contains the reagents for the reaction, for example a forward primer, a reverse primer, dNTPs, a buffer, and a DNA polymerase.

In one embodiment, the method of the invention is performed using a single RT-PCR reagent mix containing the reagents for the reverse transcription and amplification reactions. Preferably, the reverse primer used for the reverse transcription reaction is also used for the amplification reaction.

Preferably, the reverse transcription and amplification reactions are performed in a plastic or glass container, most preferably in the same container.

Amplification methods known in the art include RCA, MDA, NASBA, TMA, SDA, LCR, b-DNA, PCR (all forms including RT-PCR), RAM, LAMP, ICAN, SPIA, QB-replicase, or Invader. A preferred amplification method is the polymerase chain reaction (PCR) amplification. See, e.g., PCR Technology: Principles and Applications for DNA Amplification (Ed. H. A. Erlich, Freeman Press, NY, N.Y., 1992); PCR Protocols: A Guide to Methods and Applications (Eds. Iinis, et al., Academic Press, San Diego, Calif., 1990); Mattila et al., Nucleic Acids Res. 19, 4967 (1991); Eckert al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675. More preferred PCR methods is real-time PCR, PCR-HRM (High-Resolution DNA Melting) (see Andriantsoanirina et al. Journal of Microbiological Methods, 78: 165 (2009)) and PCR coupled to ligase detection reaction based on fluorescent microsphere (Luminex® microspheres).

Amplification techniques include in particular isothermal methods and PCR-based techniques. Isothermal techniques include such methods as nucleic acid sequence-based amplification (NASBA), loop-mediated isothermal amplification (LAMP), helicase-dependent amplification (HDA), rolling circle amplification (RCA), and strand displacement amplification (SDA), exponential amplification reaction (EX-PAR), isothermal and chimeric primer-initiated amplification of nucleic acids (ICANs), signal-mediated amplification of RNA technology (SMART) and others (see e.g. Asiello and Baeumner, Lab Chip; 11(8): 1420-1430, 2011).

Preferably, the PCR technique quantitatively measures starting amounts of DNA, cDNA, or RNA. Examples of PCR-based techniques according to the invention include techniques such as, but not limited to, quantitative PCR (Q-PCR), reverse-transcriptase polymerase chain reaction (RT-PCR), quantitative reverse-transcriptase PCR (QRT-PCR), or digital PCR. These techniques are well known and easily available technologies for those skilled in the art.

Preferably, the method is a one-step real-time RT-PCR assay, for example, as described in the Examples.

Preferably, a probe is used to detect the amplified product. The probe can be labeled with a fluorescent, radioactive, or enzymatic label. The amplified product can be detected with a specific detection chemistry such as fluorescence resonance energy transfer (FRET) probes, TAQMAN probes, molecular beacons, scorpion probes, fluorescently labeled (or other labeled) primers, lightup probes or a dye-based chemistry, DNA, PNA, LNA, or RNA including modified bases that bind to the amplified product to detect the sequence of interest.

Detection of the amplified products can be real-time (during the amplification process) or endpoint (after the amplification process). The invention allows for detection of the amplification products in the same vessel as amplification occurs.

Preferably, a DNA internal control is used to monitor the amplification reaction.

Preferably, a RNA internal control is used to monitor the reverse transcription and amplification reactions.

Primers

The primers of the invention are useful for both reverse transcription of RNA and amplification of the resultant products. The primer sequences are selective to SARS-CoV-2 within the coronaviruses and also other prevalent viruses causing respiratory diseases. The invention encompasses a set of primers, i.e., at least two primers of different orientations. Preferably, the primers are in a set of one forward primer and one reverse primer. All of the primers referred to herein can be specifically included in this set of primers.

Reverse Primers

The "reverse primer" is an anti-sense primer, which can be the primer for reverse transcription, and is conserved among coronavirus strains. Preferably, the reverse primer is specific for SARS-CoV-2.

In some embodiments, the reverse primer hybridizes to the sequence: 5'-ACAACACAACAAAGGGAG-3' (SEQ ID NO:11) and the RNA equivalent thereof or the sequence: 5'-CCTATATTAACCTTGACCAG-3' (SEQ ID NO:14) and the RNA equivalent thereof.

In a preferred embodiment, the primer for reverse transcription comprises the sequence 5'-CTCCCTTTGTTGTGTTGT-3' (SEQ ID NO: 2), or a variant thereof, and is from 15 to 21 bases in length, or comprises the sequence 5'-CTGGTCAAGGT-TAATATAGG-3' (SEQ ID NO: 5), or a variant thereof, and is from 17 to 23 bases in length. Preferably, the primer consists of the sequence 5'-CTCCCTTTGTTGTGTTGT-3' (SEQ ID NO: 2) or consists of the sequence 5'-CTGGT-CAAGGTTAATATAGG-3' (SEQ ID NO: 5).

In this context, the term "hybridizes to" refers to the ability of the primer to form a double-stranded hybrid molecule with SARS-CoV-2 RNA (i.e., comprising the RNA equivalent of SEQ ID NO:11 or 14) sufficient to produce a cDNA and to promote amplification of the cDNA under standard reverse transcription and amplification conditions such as those set forth in the example.

In various embodiments, the primer consists of or comprises the sequence: 5'-CTCCCTTTGTTGTGTTGT-3' (SEQ ID NO: 2) or 5'-CTGGTCAAGGTTAATATAGG-3' (SEQ ID NO: 5).

In various embodiments, the primer is at least 12, 13, 14, 15, 16, 17, 18, 19, 20, 21, 22, 23, 24, 25, 26, 27, 28, 29, or 30 nucleotides in length.

In various embodiments, the primer comprises the sequence: 5'-CTCCCTTTGTTGTGTTGT-3' (SEQ ID NO: 2) or 5'-CTGGTCAAGGTTAATATAGG-3' (SEQ ID NO: 5), in which at least 1, 2, 3, 4, or 5 nucleotides are added at the 5' end and/or at least 1, 2, 3, 4, or 5 nucleotides are added at the 3' end.

Forward Primers

The "forward primer" is a sense primer, which is specific for a subset of SARS-CoV-2.

In some embodiments, the forward primer hybridizes to the sequence: 5'-CAACAGGACTAAGCTCAT-3' (SEQ ID NO: 10) or the sequence: 5'-CGAAATCATACCAGTTACC-3' (SEQ ID NO:13).

In a preferred embodiment, the forward primer comprises the sequence 5'-ATGAGCTTAGTCCTGTTG-3' (SEQ ID NO: 1), or a variant thereof, that is from 15 to 21 bases in length, or comprises the sequence 5'-GGTAACTGGTAT-GATTTCG-3' (SEQ ID NO: 4), or a variant thereof, and is from 16 to 22 bases in length. Preferably, the primer consists of the sequence 5'-ATGAGCTTAGTCCTGTTG-3' (SEQ ID NO: 1) or consists of the sequence 5'-GGTAACTGGTATGATTTCG-3' (SEQ ID NO: 4).

In this context, the term "hybridizes to" refers to the ability of the primer to form a double-stranded hybrid molecule with SARS-CoV-2 RNA (i.e., comprising the RNA equivalent of SEQ ID NO:10 or 13) sufficient to produce a cDNA and to promote amplification of the cDNA under standard reverse transcription and amplification conditions such as those set forth in the example.

In various embodiments, the primer consists of or comprises the sequence: 5'-ATGAGCTTAGTCCTGTTG-3' (SEQ ID NO: 1) or 5'-GGTAACTGGTATGATTTCG-3' (SEQ ID NO: 4).

In various embodiments, the primer is at least 12, 13, 14, 15, 16, 17, 18, 19, 20, 21, 22, 23, 24, 25, 26, 27, 28, 29, or 30 nucleotides in length.

In various embodiments, the primer comprises the sequence: 5'-ATGAGCTTAGTCCTGTTG-3' (SEQ ID NO: 1) or 5'-GGTAACTGGTATGATTTCG-3' (SEQ ID NO: 4), in which at least 1, 2, 3, 4, or 5 nucleotides are added at the 5' end and/or at least 1, 2, 3, 4, or 5 nucleotides are added at the 3' end.

In some embodiments, the reverse and forward primers amplify a target sequence of SARS-CoV-2 RNA selected from the group consisting of the sequence SEQ ID NO: 16 and SEQ ID NO: 17 and the variants thereof comprising the addition of up to 20 consecutive nucleotides of 5' and/or 3' flanking sequence from said SARS-CoV-2 RNA or the deletion of up to 20 consecutive nucleotides at one or both ends of said sequences. The variant comprises the addition or deletion of up to 20 consecutive nucleotides (2, 3, 4, 5, 6, 7, 8, 9, 10, 11, 12, 13, 14, 15, 16, 17, 18, 19 and 20), preferably up to 15 (2, 3, 4, 5, 6, 7, 8, 9, 10, 11, 12, 13, 14, 15), up to 10 (2, 3, 4, 5, 6, 7, 8, 9, 10) or up to 5 (2, 3, 4, 5) consecutive nucleotides. The primer (reverse or forward) hybridizes to the target sequence or complement thereof and can be further extended in the presence of a nucleic acid polymerase to specifically amplify the target sequence. The primer sequence is substantially complementary to the target sequence or its complement. Substantially complementary means that the primer sequence is at least 80% identical, preferably at least 85%, 90%, 95% and 98% identical to the target sequence or its complement. The primer may comprise additional sequences (not complementary to the target sequence) at its 5' end. In some embodiments the primer comprises a sequence of at least 5, preferably 10 to 15 consecutive nucleotides which is 100% identical to the target sequence or its complement. In some more preferred embodiments, the primer sequence is 100% identical to the target sequence or its complement. Optionally, at least one primer of the pair includes a label (detectable moiety). In some more preferred embodiments, the reverse and forward primer is as described above.

Probes

The probes of the invention are useful for detection of coronavirus nucleic acids. As referred to herein, the "probe" of the invention is linked to a detectable label suitable for use in the method the invention. The probe is specific for SARS-CoV-2 strains.

A "detectable label" as used herein is a moiety, which can be detected directly or indirectly. In some embodiments, detection of the label involves directly detecting an emission of energy by the label (e.g., radioactivity, luminescence, optical). A label can also be detected indirectly by its ability to bind to or cleave another moiety, which itself may emit or absorb light of a particular wavelength (e.g., biotin, avidin, epitope tag such as the FLAG epitope, enzyme tag such as horseradish peroxidase). Preferred detectable labels include radioactive labels, fluorescent labels, chemiluminescent labels, bioluminescent labels, and epitope tags. Preferably, the probe is labelled with the fluorescent dyes 6-carboxy-fluorescein (6FAM) or hexachloro-6-carboxy-fluorescein (HEX), most preferably at the 5 'end. Preferably, the probe is labelled at its 3' end with black hole quencher 1 (BHQ1).

In a preferred embodiment, the probe hybridizes to the sequence: 5'-TACCGGCAGCACAAGACATCT-3' (SEQ ID NO:12) or the complement thereof, or to the sequence 5'-CCTGGCGTGGTTTGTATGA-3' (SEQ ID NO:15) or the complement thereof.

In preferred embodiments, the probe consists of or comprises the sequence: 5'-AGATGTCTTGTGCTGCCGGTA-3' (SEQ ID NO: 3), or a variant thereof, or the complement thereof and is at least 15, 16, 17, 18, 19, 20, 21, 22, 23, 24, 25, 26, 27, 28, 29, or 30 nucleotides long.

In preferred embodiments, the probe consists of or comprises the sequence: 5'-TCATACAAACCACGCCAGG-3' (SEQ ID NO: 6), or a variant thereof, or the complement thereof and is at least 15, 16, 17, 18, 19, 20, 21, 22, 23, 24, 25, 26, 27, 28, 29, or 30 nucleotides long.

In various embodiments, the probe is at least 15, 16, 17, 18, 19, 20, 21, 22, 23, 24, 25, 26, 27, 28, 29, or 30 nucleotides in length.

Controls

In various embodiments, the invention encompasses the inclusion of controls for the reverse transcription and/or amplification reactions. The DNA control of the invention is useful to monitor the amplification reaction.

In various embodiments, the control is an internal positive control, for example, wherein the internal positive control reverse primer comprises the sequence 5'-ATATTGCAGCAGTACGCACACA-3' (SEQ ID NO: 8), or a variant thereof, and is from 19 to 25 bases in length; and/or wherein the internal positive control forward primer comprises the sequence 5'-ACAGGTACGTTAATAGTTAATAGCGT-3' (SEQ ID NO: 7), or a variant thereof, and is from 23 to 29 bases in length; and/or wherein the internal positive control probe comprises the sequence 5'-ACACTAGCCATCCTTACTGCGCTTCG-3' (SEQ ID NO: 9), or a variant thereof, or the complement thereof, and is from 23 to 29 bases in length.

In some embodiments, a real-time RT-PCR assay includes in addition of unknown samples:

Two negative samples bracketing unknown samples during RNA extraction (negative extraction controls); and/or Positive controls (in duplicate); when using in vitro synthesized transcripts as controls include five quantification positive controls (in duplicate) including $10^5$, $10^4$ and $10^3$ copies genome equivalent (ge) of in vitro synthesized RNA transcripts; and/or one negative amplification control.

Kits

The kits of the invention are useful for the reverse transcription of RNA, the amplification of the resultant products, and the detection of SARS-CoV-2 nucleic acids. The kits can contain reagents for each of these reactions. The kits of the invention can contain any of the primers, controls, and probes of the invention, alone or in any and all combinations.

In various embodiments, the kit comprises buffer(s), a reverse transcriptase, a DNA polymerase, dNTPs, primer(s), probe(s), and/or an internal control(s).

The primers, probes and kits according to the invention and as described above can be practiced on different samples; human and non-human animals, surfaces, soils, for diagnostic, epidemiology, surveillance, as well as to screen blood and tissue banks which may need to be tested against SARS-CoV2 as part of the screening for HIV1, HIV2, HBV, HCV, etc.

Examples

1. Detection of SARS-CoV-2

This protocol describes procedures for the detection of SARS-CoV-2 for two RdRp targets (IP2 and IP4). Based on the first sequences of SARS-CoV-2 made available on the GISAID database on Jan. 11, 2020 (SEQ ID NO: 19), primers and probes (nCoV_IP2 and nCoV_IP4) were designed to target the RdRp gene spanning nt 12621-12727 and 14010-14116 (positions according SARS-CoV, NC_004718). These positions correspond to nt 12669-12776 and 14059-14165 in SARS-CoV-2 sequence (SEQ ID NO: 19).

As a confirmatory assay, the E gene assay from the Charité protocol was used. (Corman V M, Landt O, Kaiser M, et al. Detection of 2019 novel coronavirus (2019-nCoV) by real-time RT-PCR. Euro Surveill 2020; 25.)

A. Kits

Kit Extraction NucleoSpin Dx Virus (Macherey Nagel 740895.50).

SuperScript™ III Platinum® One-Step Quantitative RT-PCR System. (Invitrogen 1732-020.)

B. Primers and Probes

E gene: 26141-26253. The amplicon (113 bp) has the sequence SEQ ID NO: 18 which corresponds to positions 26249-26361 in SARS-CoV-2 sequence (SEQ ID NO: 19).

C. Nucleic Acid Extraction

RNA is extracted from specimens using the NucleoSpin Dx Virus (Macherey Nagel ref. 740895.50). RNA extracted from 100 µl of original sample, is eluted in 100 µl of elution buffer.

D. Mix Preparation for all Separate Primer/Probe Combinations

All primers and probes described below were validated under the following conditions.

RT-PCR Mix kit: Invitrogen Superscript™ III Platinum® One-Step qRT-PCR system (ref: 11732-088).

Real-time PCR equipment: LightCycler 480 (96).

Adjustments may be required for the use of other kits or other real-time PCR instruments. All Assays used the same conditions. Primer and probe sequences, as well as optimized concentrations are shown in table below. A 25 µl reaction was set up containing 5 µl of RNA.

| Simplex Mix | Vol (µl) | [final] |
|---|---|---|
| $H_2O$ PPI | 3.60 | |
| Reaction mix 2X | 12.50 | 3 mM Mg |
| $MgSO_4$ (50 mM) | 0.40 | 0.8 mM Mg |
| Forward Primer (10 µM) | 1.00 | 0.4 µM |

| Name | Sequences (5'-3') | Length (bases) | PCR product size | Ref. |
|---|---|---|---|---|
| RdRp gene/nCoV_IP2 | | | | |
| nCoV_IP2-12669Fw | ATGAGCTTAGTCCTGTTG (SEQ ID NO: 1) | 18 | 108 bp | 1 |
| nCoV_IP2-12759Rv | CTCCCTTTGTTGTGTTGT (SEQ ID NO: 2) | 18 | | |
| nCoV_IP2-12696bProbe(+) | AGATGTCTTGTGCTGCCGGTA [5']Hex[3']BHQ-1 (SEQ ID NO: 3) | 21 | | |
| RdRp gene/nCoV_IP4 | | | | |
| nCoV_IP4-14059Fw | GGTAACTGGTATGATTTCG (SEQ ID NO: 4) | 19 | 107 bp | 1 |
| nCoV_IP4-14146Rv | CTGGTCAAGGTTAATATAGG (SEQ ID NO: 5) | 20 | | |
| nCoV_IP4-14084Probe(+) | TCATACAAACCACGCCAGG [5']Fam[3']BHQ-1 (SEQ ID NO: 6) | 19 | | |
| E gene/E_Sarbeco (CoVE) | | | | |
| E_Sarbeco_F1 | ACAGGTACGTTAATAGTTAATAGCGT (SEQ ID NO: 7) | 26 | 113 bp | 2 |
| E_Sarbeco_R2 | ATATTGCAGCAGTACGCACACA (SEQ ID NO: 8) | 22 | | |
| E_Sarbeco_P1 | ACACTAGCCATCCTTACTGCGCTTCG[5']Fam[3']BHQ-1 (SEQ ID NO: 9) | 26 | | |

1 National Reference Center for Respiratory Viruses, Institut Pasteur, Paris.
2 Corman VM, Landt O, Kaiser M, et al. Detection of 2019 novel coronavirus (2019-nCoV) by real-time RT-PCR. Euro Surveill 2020;25.

Primer sets nCoV_IP2 and nCoV_IP4 can be multiplexed. Both reaction mixtures are described below.

PCR amplification regions (positions according to SARS-CoV, NC_004718):

nCoV_IP2: 12621-12727. The amplicon (108 bp) has the sequence SEQ ID NO: 16 which corresponds to positions 12669-12776 in SARS-CoV-2 sequence (SEQ ID NO: 19)

nCoV_IP4: 14010-14116. The amplicon (107 bp) has the sequence SEQ ID NO: 17 which corresponds to positions 14059-14165 in SARS-CoV-2 sequence (SEQ ID NO: 19)

| Simplex Mix | Vol (µl) | [final] |
|---|---|---|
| -continued | | |
| Reverse Primer 10 µM | 1.00 | 0.4 µM |
| Probe (10 µM) | 0.50 | 0.2 µM |
| SuperscriptIII RT/Platinum Taq Mix | 1.00 | |
| Final Volume | 20.00 | |

| Multiplex Mix (nCoV_IP2&IP4) | Vol (μl) | [final] |
|---|---|---|
| H₂O PPI | 1.3 | |
| Reaction mix 2X | 12.50 | 3 mM Mg |
| MgSO₄ (50 mM) | 0.40 | 0.8 mM Mg |
| Forward Primer (10 μM) | 1.00 | 0.4 μM |
| Reverse Primer (10 μM) | 1.00 | 0.4 μM |
| Forward Primer (10 μM) | 1.00 | 0.4 μM |
| Reverse Primer (10 μM) | 1.00 | 0.4 μM |
| Probe (10 μM) | 0.4 | 0.16 μM |
| Probe (10 μM) | 0.4 | 0.16 μM |
| SuperscriptIII RT/Platinum Taq Mix | 1.00 | |
| Final Volume | 20.00 | |

E. Controls

Each real-time RT-PCR assay includes in addition of unknown samples:

Two negative samples bracketing unknown samples during RNA extraction (negative extraction controls).

Positive controls (in duplicate); when using in vitro synthesized transcripts as controls include five quantification positive controls (in duplicate) including $10^5$, $10^4$ and $10^3$ copies genome equivalent (ge) of in vitro synthesized RNA transcripts.

One negative amplification control.

F. Amplification Cycles (Lightcycler System)

| | | | | |
|---|---|---|---|---|
| Reverse transcription | 55° C. | 20 min | ×1 | |
| Denaturation | 95° C. | 3 min | ×1 | |
| Amplification | 95° C. | 15 sec | ×50 | Acquisition |
| | 58° C. | 30 sec | | |
| Cooling | 40° C. | 30 sec | ×1 | |

G. Sensitivity nCoV_IP and E_Sarbeco Real-Time RT-PCR

Sensitivity, in terms of 95% hit rate is about 100 copies of RNA genome equivalent per reaction (this amount of target sequences is always detected), the probability to detect lower amounts of virus decreases, but samples containing 10 copies could be detected with multiplex assay.

| RNA copies Of transcript | Multiplex (Ct values) | | Simplex (Ct values) |
|---|---|---|---|
| | nCoV_IP2 | nCoV_IP4 | E_Sarbeco |
| 1.00E+07 | 21.67 | 21.97 | 24.72 |
| 1.00E+06 | 24.97 | 25.12 | 28.19 |
| 1.00E+05 | 28.00 | 27.88 | 30.96 |
| 1.00E+04 | 31.84 | 30.51 | 33.33 |

Ct values may vary from instrument to instrument by up to 2 cycles, while the interval between two dilutions steps is constant (ΔCt).

H. Specificity

Cross-reactivity with other respiratory viruses was tested with specimens known to be positive for a panel of respiratory viruses (influenza A(H1N1)pdm09, A(H3N2), B-Victoria, B-Yamagata; influenza C; RSV A, B; hBoV; hPIV; hMPV; HRV/enterovirus; adenovirus; hCoV (HKU1, OC43, 229E and NL63); MERS-CoV. None of the tested viruses showed reactivity with PCR2 and PCR4 using the IP2 and IP4 sets of primers and probes described in the Table above.

I. Positive Control for SARS-CoV-2 Real Time RT-PCR

Positive control for real-time RT-PCR is an in vitro transcribed RNA derived from strain BetaCoV_Wuhan_WIV04_2019 (EPI_ISL_402124). The transcript contains the amplification regions of the RdRp and E gene as positive strand. Each microtube contains 1011 copies of target sequences diluted in yeast tRNA, and lyophilised.

Reconstitution of Transcribed RNA

Add 100 μl of RNase/DNAse-free H2O to obtain a solution at a concentration of 109 copies/μl. Store at −80° C. Dilute to prepare a master bank at 2×106 copies/μl. Store at −80° C.

From this prepare a working bank of reagent at 2×104 copies/μl in order to avoid freeze/thaw cycles. Working tubes may be stored at −20° C. for less than one week.

This test which is now validated on a panel of SARS-CoV-2 of 600 positive and negative patients, including asymptomatic contact individuals, individuals returning from epidemic zone, and symptomatic patients. Within symptomatic patients, as there is also a concurrent epidemic of flu in France, negative patients with the SARS-CoV2 test of the invention were confirmed to be infected by flu or other respiratory diseases. The validation of this test will now allow dispatch for diagnosis to reference hospitals in France and abroad, and within the international network of Institut Pasteur around the world.

The invention claimed is:

1. A method for specific detection of the presence or absence of a SARS-CoV-2 RNA in a sample, comprising:
   providing a sample; and
   subjecting the sample to a reverse transcription reaction with a reverse primer to generate a cDNA copy of SARS-CoV-2 RNA in the sample, amplifying any resultant cDNA, and detecting any amplified product with a probe,
   wherein the reverse primer comprises the sequence 5'-CTGGTCAAGGTTAATATAGG-3' (SEQ ID NO: 5) or a variant thereof, and is from 17 to 23 bases in length; and/or
   wherein the forward primer comprises the sequence 5'-GGTAACTGGTATGATTTCG-3' (SEQ ID NO: 4), or a variant thereof, and is from 16 to 22 bases in length; and/or
   wherein the probe comprises the sequence 5'-TCATACAAACCACGCCAGG-3' (SEQ ID NO: 6), or a variant thereof, or the complement of either of these, and is from 16 to 22 bases in length.

2. The method of claim 1,
   wherein the reverse primer consists of the sequence 5'-CTGGTCAAGGTTAATATAGG-3' (SEQ ID NO: 5); and/or
   wherein the forward primer consists of the sequence 5'-GGTAACTGGTATGATTTCG-3' (SEQ ID NO: 4); and/or
   wherein the probe consists of the sequence 5'-TCATACAAACCACGCCAGG-3' (SEQ ID NO: 6), or the complement thereof.

3. The method of claim 2,
   wherein the reverse primer consists of the sequence 5'-CTGGTCAAGGTTAATATAGG-3' (SEQ ID NO: 5);
   wherein the forward primer consists of the sequence 5'-GGTAACTGGTATGATTTCG-3' (SEQ ID NO: 4); and
   wherein the probe consists of the sequence 5'-TCATACAAACCACGCCAGG-3' (SEQ ID NO: 6), or the complement thereof.

4. The method of claim 1, wherein the presence of the amplified product is detected.

5. The method of claim 1, wherein the absence of the amplified product is detected.

6. The method of claim 1, wherein the method is an RT-PCR method.

7. The method of claim 1, wherein the method comprises reverse transcribing and amplifying an internal positive control, and detecting an amplified internal positive control product with a probe.

8. The method of claim 7,
   wherein the reverse transcribing and amplifying is performed using an internal positive control reverse primer comprising the sequence 5'-ATATGCAGCAGTACGCACACA-3' (SEQ ID NO: 8), or a variant thereof, that is from 19 to 25 bases in length; and/or
   an internal positive control forward primer comprising the sequence 5'-ACAGGTACGTTAATAGTTAATAGCGT-3' (SEQ ID NO: 7), or a variant thereof, that is from 23 to 29 bases in length; and/or
   an internal positive control probe comprising the sequence 5'-ACACTAGCCATCCTTACTGCGCTTCG-3' (SEQ ID NO: 9), or the complement thereof, that is from 23 to 29 bases in length.

9. The method of claim 8, wherein the probe and the internal positive control probe are labelled with 6-carboxyfluorescein (6FAM) or hexachloro-6-carboxy-fluorescein (HEX) at the 5' end.

10. The method of claim 8, wherein the probe and the internal positive control probe are labelled with black hole quencher 1 (BHQ1) at the 3' end.

* * * * *

SEQUENCE LISTING

<160> NUMBER OF SEQ ID NOS: 19

<210> SEQ ID NO 1
<211> LENGTH: 18
<212> TYPE: DNA
<213> ORGANISM: artificial sequence
<220> FEATURE:
<223> OTHER INFORMATION: synthetic oligonucleotide (forward primer nCoV_IP2-12669Fw)

<400> SEQUENCE: 1
atgagcttag tcctgttg          18

<210> SEQ ID NO 2
<211> LENGTH: 18
<212> TYPE: DNA
<213> ORGANISM: artificial sequence
<220> FEATURE:
<223> OTHER INFORMATION: synthetic oligonucleotide (reverse primer nCoV_IP2-12759Rv)

```
<400> SEQUENCE: 2 ctcccttgt tgtgttgt                                                      18

<210> SEQ ID NO 3
<211> LENGTH: 21
<212> TYPE: DNA
<213> ORGANISM: artificial sequence
<220> FEATURE:
<223> OTHER INFORMATION: synthetic oligonucleotide (probe nCoV_IP2-
      12696bProbe(+))

<400> SEQUENCE: 3
agatgtcttg tgctgccggt a                                                 21

<210> SEQ ID NO 4
<211> LENGTH: 19
<212> TYPE: DNA
<213> ORGANISM: artificial sequence
<220> FEATURE:
<223> OTHER INFORMATION: synthetic oligonucleotide (forward primer
      nCoV_IP4-14059Fw)

<400> SEQUENCE: 4
ggtaactggt atgatttcg                                                    19

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide (reverse primer
      nCoV_IP4-14146Rv)

<400> SEQUENCE: 5
ctggtcaagg ttaatatagg                                                   20

<210> SEQ ID NO 6
<211> LENGTH: 19
<212> TYPE: DNA
<213> ORGANISM: artificial sequence
<220> FEATURE:
<223> OTHER INFORMATION: synthetic oligonucleotide (probe nCoV_IP4-
      14084Probe(+))

<400> SEQUENCE: 6
tcatacaaac cacgccagg                                                    19

<210> SEQ ID NO 7
<211> LENGTH: 26
<212> TYPE: DNA
<213> ORGANISM: artificial sequence
<220> FEATURE:
<223> OTHER INFORMATION: synthetic oligonucleotide (forward primer
      E_Sarbeco_F1)

<400> SEQUENCE: 7
acaggtacgt taatagttaa tagcgt                                            26

<210> SEQ ID NO 8
<211> LENGTH: 22
<212> TYPE: DNA
<213> ORGANISM: artificial sequence
<220> FEATURE:
<223> OTHER INFORMATION: synthetic oligonucleotide (reverse primer
      E_Sarbeco_R2)
```

```
<400> SEQUENCE: 8
atattgcagc agtacgcaca ca                                             22

<210> SEQ ID NO 9
<211> LENGTH: 26
<212> TYPE: DNA
<213> ORGANISM: artificial sequence
<220> FEATURE:
<223> OTHER INFORMATION: synthetic oligonucleotide (probe E_Sarbeco_P1)

<400> SEQUENCE: 9
acactagcca tccttactgc gcttcg                                         26

<210> SEQ ID NO 10
<211> LENGTH: 18
<212> TYPE: DNA
<213> ORGANISM: artificial sequence
<220> FEATURE:
<223> OTHER INFORMATION: synthetic oligonucleotide (target sequence)

<400> SEQUENCE: 10
caacaggact aagctcat                                                  18

<210> SEQ ID NO 11
<211> LENGTH: 18
<212> TYPE: DNA
<213> ORGANISM: artificial sequence
<220> FEATURE:
<223> OTHER INFORMATION: synthetic oligonucleotide (target sequence)

<400> SEQUENCE: 11
acaacacaac aaagggag                                                  18

<210> SEQ ID NO 12
<211> LENGTH: 21
<212> TYPE: DNA
<213> ORGANISM: artificial sequence
<220> FEATURE:
<223> OTHER INFORMATION: synthetic oligonucleotide (target sequence)

<400> SEQUENCE: 12
taccggcagc acaagacatc t                                              21

<210> SEQ ID NO 13
<211> LENGTH: 19
<212> TYPE: DNA
<213> ORGANISM: artificial sequence
<220> FEATURE:
<223> OTHER INFORMATION: synthetic oligonucleotide (target sequence)

<400> SEQUENCE: 13
cgaaatcata ccagttacc                                                 19

<210> SEQ ID NO 14
<211> LENGTH: 20
<212> TYPE: DNA
<213> ORGANISM: artificial sequence
<220> FEATURE:
<223> OTHER INFORMATION: synthetic oligonucleotide (target sequence)

<400> SEQUENCE: 14
cctatattaa ccttgaccag                                                20

<210> SEQ ID NO 15
<211> LENGTH: 19
```

```
<212> TYPE: DNA
<213> ORGANISM: artificial sequence
<220> FEATURE:
<223> OTHER INFORMATION: synthetic oligonucleotide (target sequence)

<400> SEQUENCE: 15
cctggcgtgg tttgtatga                                                    19

<210> SEQ ID NO 16
<211> LENGTH: 108
<212> TYPE: DNA
<213> ORGANISM: artificial sequence
<220> FEATURE:
<223> OTHER INFORMATION: synthetic polynucleotide (nCoV_IP2
      amplification product)

<400> SEQUENCE: 16
atgagcttag tcctgttgca ctacgacaga tgtcttgtgc tgccggtact acacaaactg       60
cttgcactga tgacaatgcg ttagcttact acaacacaac aaagggag                   108

<210> SEQ ID NO 17
<211> LENGTH: 107
<212> TYPE: DNA
<213> ORGANISM: artificial sequence
<220> FEATURE:
<223> OTHER INFORMATION: synthetic polynucleotide (nCoV_IP4
      amplification product)

<400> SEQUENCE: 17
ggtaactggt atgatttcgg tgatttcata caaaccacgc caggtagtgg agttcctgtt       60
gtagattctt attattcatt gttaatgcct atattaacct tgaccag                   107

<210> SEQ ID NO 18
<211> LENGTH: 113
<212> TYPE: DNA
<213> ORGANISM: artificial sequence
<220> FEATURE:
<223> OTHER INFORMATION: synthetic polynucleotide (E_Sarbeco
      amplification product)

<400> SEQUENCE: 18
acaggtacgt taatagttaa tagcgtactt cttttcttg ctttcgtggt attcttgcta        60
gttacactag ccatccttac tgcgcttcga ttgtgtgcgt actgctgcaa tat            113

<210> SEQ ID NO 19
<211> LENGTH: 29788
<212> TYPE: DNA
<213> ORGANISM: SARS-CoV-2

<400> SEQUENCE: 19
aggtaacaaa ccaaccaact ttcgatctct tgtagatctg ttctctaaac gaactttaaa       60
atctgtgtgg ctgtcactcg gctgcatgct tagtgcactc acgcagtata attaataact     120
aattactgtc gttgacagga cacgagtaac tcgtctatct tctgcaggct gcttacggtt     180
tcgtccgtgt tgcagccgat catcagcaca tctaggtttc gtccgggtgt gaccgaaagg     240
taagatggag agccttgtcc ctggtttcaa cgagaaaaca cacgtccaac tcagtttgcc     300
tgttttacag gttcgcgacg tgctcgtacg tggctttgga gactccgtgg aggaggtctt     360
atcagaggca cgtcaacatc ttaaagatgg cacttgtggc ttagtagaag ttgaaaaagg     420
cgttttgcct caacttgaac agccctatgt gttcatcaaa cgttcggatg ctcgaactgc     480
acctcatggt catgttatgg ttgagctggt agcagaactc gaaggcattc agtacggtcg     540
```

```
tagtggtgag acacttggtg tccttgtccc tcatgtgggc gaaataccag tggcttaccg    600
caaggttctt cttcgtaaga acggtaataa aggagctggt ggccatggtt acggcgccga    660
tctaaagtca tttgacttag gcgacgagct tggcactgat ccttatgaag attttcaaga    720
aaactggaac actaaacata gcagtggtgt tacccgtgaa ctcatgcgtg agcttaacgg    780
aggggcatac actcgctatg tcgataacaa cttctgtggc cctgatggct accctcttga    840
gtgcattaaa gaccttctag cacgtgctgg taaagcttca tgcactttgt ccgaacaact    900
ggactttatt gacactaaga ggggtgtata ctgctgccgt gaacatgagc atgaaattgc    960
ttggtacacg gaacgttctg aaaagagcta tgaattgcag acaccttttg aaattaaatt   1020
ggcaaagaaa tttgacacct tcaatgggga atgtccaaat tttgtatttc ccttaaattc   1080
cataatcaag actattcaac caaggggtga aaagaaaaag cttgatggct ttatgggtag   1140
aattcgatct gtctatccag ttgcgtcacc aaatgaatgc aaccaaatgt gcctttcaac   1200
tctcatgaag tgtgatcatt gtggtgaaac ttcatggcag acgggcgatt tgttaaagc    1260 cacttgcgaa ttttgtggca ctgagaattt gactaaagaa ggtgccacta cttgtggtta   1320
cttaccccaa aatgctgttg ttaaaattta ttgtccagca tgtcacaatt cagaagtagg   1380
acctgagcat agtcttgccg aataccataa tgaatctggc ttgaaaacca ttcttcgtaa   1440
gggtggtcgc actattgcct ttggaggctg tgtgttctct tatgttggtt gccataacaa   1500
gtgtgcctat tgggttccac gtgctagcgc taacataggt tgtaaccata caggtgttgt   1560
tggagaaggt tccgaaggtc ttaatgacaa ccttcttgaa atactccaaa agagaaagt    1620 caacatcaat attgttggtg actttaaact taatgaagag atcgccatta ttttggcatc   1680 ttttttctgct tccacaagtg cttttgtgga aactgtgaaa ggtttggatt ataaagcatt   1740
caaacaaatt gttgaatcct gtggtaattt taaagttaca aaaggaaaag ctaaaaaagg   1800
tgcctggaat attggtgaac agaaatcaat actgagtcct ctttatgcat ttgcatcaga   1860
ggctgctcgt gttgtacgat caattttctc ccgcactctt gaaactgctc aaaattctgt   1920
gcgtgtttta cagaaggccg ctataacaat actagatgga atttcacagt attcactgag   1980
actcattgat gctatgatgt tcacatctga tttggcactac aacaatctag ttgtaatggc   2040
ctacattaca ggtggtgttg ttcagttgac ttcgcagtgg ctaactaaca tctttggcac   2100
tgtttatgaa aaactcaaac ccgtccttga ttggcttgaa gagaagttta aggaaggtgt   2160
agagtttctt agagacggtt gggaaattgt taaatttatc tcaacctgtg cttgtgaaat   2220
tgtcggtgga caaattgtca cctgtgcaaa ggaaattaag gagagtgttc agacattctt   2280
taagcttgta aataaatttt tggctttgtg tgctgactct atcattattg gtggagctaa   2340
acttaaagcc ttgaatttag gtgaaacatt tgtcacgcac tcaaagggat tgtacagaaa   2400
gtgtgttaaa tccagagaag aaactggcct actcatgcct ctaaaagccc caaagaaat    2460 tatcttctta gagggagaaa cacttcccac agaagtgtta acagaggaag ttgtcttgaa   2520
aactggtgat ttacaaccat tagaacaacc tactagtgaa gctgttgaag ctccattggt   2580
tggtacacca gtttgtatta acgggcttat gttgctcgaa atcaaagaca cagaaaagta   2640 ctgtgcccctt gcacctaata tgatggtaac aaacaatacc ttcacactca aaggcggtgc   2700
accaacaaag gttacttttg gtgatgacac tgtgatagaa gtgcaaggtt acaagagtgt   2760
gaatatcact tttgaacttg atgaaaggat tgataaagta cttaatgaga gtgctctgc    2820 ctatacagtt gaactcggta cagaagtaaa tgagttcgcc tgtgttgtgg cagatgctgt   2880
```

```
cataaaaact ttgcaaccag tatctgaatt acttacacca ctgggcattg atttagatga    2940
gtggagtatg gctacatact acttatttga tgagtctggt gagtttaaat tggcttcaca    3000
tatgtattgt tctttctacc ctccagatga ggatgaagaa gaaggtgatt gtgaagaaga    3060
agagtttgag ccatcaactc aatatgagta tggtactgaa gatgattacc aaggtaaacc    3120
tttggaattt ggtgccactt ctgctgctct tcaacctgaa gaagagcaag aagaagattg    3180
gttagatgat gatagtcaac aaactgttgg tcaacaagac ggcagtgagg acaatcagac    3240
aactactatt caaacaattg ttgaggttca acctcaatta gagatggaac ttacaccagt    3300
tgttcagact attgaagtga atagttttag tggttattta aaacttactg acaatgtata    3360
cattaaaaat gcagacattg tggaagaagc taaaaaggta aaaccaacag tggttgttaa    3420
tgcagccaat gtttacctta acatggagg aggtgttgca ggagccttaa ataaggctac     3480
taacaatgcc atgcaagttg aatctgatga ttacatagct actaatggac cacttaaagt    3540
gggtggtagt tgtgttttaa gcggacacaa tcttgctaaa cactgtcttc atgttgtcgg    3600
cccaaatgtt aacaaaggtg aagacattca acttcttaag agtgcttatg aaaattttaa    3660
tcagcacgaa gttctacttg caccattatt atcagctggt atttttggtg ctgaccctat    3720
acattcttta agagtttgtg tagatactgt tcgcacaaat gtctacttag ctgtctttga    3780
taaaaatctc tatgacaaac ttgtttcaag cttttttggaa atgaagagtg aaaagcaagt    3840
tgaacaaaag atcgctgaga ttcctaaaga ggaagttaag ccatttataa ctgaaagtaa    3900
accttcagtt gaacagagaa aacaagatga taagaaaatc aaagcttgtg ttgaagaagt    3960
tacaacaact ctggaagaaa ctaagttcct cacagaaaac ttgttacttt atattgacat    4020
taatggcaat cttcatccag attctgccac tcttgttagt gacattgaca tcactttctt    4080
aaagaaagat gctccatata tagtgggtga tgttgttcaa gagggtgttt taactgctgt    4140
ggttatacct actaaaaagg ctggtggcac tactgaaatg ctagcgaaag ctttgagaaa    4200
agtgccaaca gacaattata taaccactta cccgggtcag ggtttaaatg gttacactgt    4260
agaggaggca aagacagtgc ttaaaaagtg taaaagtgcc ttttacattc taccatctat    4320
tatctctaat gagaagcaag aaattcttgg aactgttttct tggaatttgc gagaaatgct    4380
tgcacatgca gaagaaacac gcaaattaat gcctgtctgt gtggaaacta agccatagt     4440 ttcaactata cagcgtaaat ataagggtat taaaatacaa gagggtgtgg ttgattatgg    4500
tgctagattt tacttttaca ccagtaaaac aactgtagcg tcacttatca acacacttaa    4560
cgatctaaat gaaactcttg ttacaatgcc acttggctat gtaacacatg cttaaatttt    4620
ggaagaagct gctcggtata tgagatctct caaagtgcca gctacagttt ctgtttcttc    4680
acctgatgct gttacagcgt ataatggtta tcttacttct tcttctaaaa cacctgaaga    4740 acatttatt gaaaccatct cacttgctgg ttcctataaa gattggtcct attctggaca     4800
atctacacaa ctaggtatag aatttcttaa gagaggtgat aaaagtgtat attacactag    4860
taatcctacc acattccacc tagatggtga agttatcacc tttgacaatc ttaagacact    4920
tctttctttg agagaagtga ggactattaa ggtgtttaca acagtagaca acattaacct    4980
ccacacgcaa gttgtggaca tgtcaatgac atatggacaa cagtttggtc caacttattt    5040
ggatggagct gatgttacta aaataaaacc tcataattca catgaaggta aacattttta    5100
tgttttacct aatgatgaca ctctacgtgt tgaggctttt gagtactacc atacaactga    5160
tcctagtttt ctgggtaggt acatgtcagc attaaatcac actaaaaagt ggaaataccc    5220
acaagttaat ggtttaactt ctattaaatg ggcagataac aactgttatc ttgccactgc    5280
```

```
attgttaaca ctccaacaaa tagagttgaa gtttaatcca cctgctctac aagatgctta    5340
ttacagagca agggctggtg aagctgctaa cttttgtgca cttatcttag cctactgtaa    5400
taagacagta ggtgagttag gtgatgttag agaaacaatg agttacttgt ttcaacatgc    5460
caatttagat tcttgcaaaa gagtcttgaa cgtggtgtgt aaaacttgtg acaacagca    5520 gacaaccctt aagggtgtag aagctgttat gtacatgggc acactttctt atgaacaatt    5580
taagaaaggt gttcagatac cttgtacgtg tggtaaacaa gctacaaaat atctagtaca    5640
acaggagtca ccttttgtta tgatgtcagc accacctgct cagtatgaac ttaagcatgg    5700
tacatttact tgtgctagtg agtacactgg taattaccag tgtggtcact ataaacatat    5760
aacttctaaa gaaactttgt attgcataga cggtgcttta cttacaaagt cctcagaata    5820
caaaggtcct attacggatg ttttctacaa agaaaacagt tacacaacaa ccataaaacc    5880
agttacttat aaattggatg gtgttgtttg tacagaaatt gaccctaagt tggacaatta    5940
ttataagaaa taccattctt atttcacaga gcaaccaatt gatcttgtac caaaccaacc    6000
atatccaaac gcaagcttcg ataattttaa gtttgtatgt gataatatca aatttgctga    6060
tgatttaaac cagttaactg gttataagaa acctgcttca agagagctta agttacatt    6120 tttccctgac ttaaatggtg atgtggtggc tattgattat aaacactaca caccctcttt    6180
taagaaagga gctaaattgt tacataaacc tattgtttgg catgttaaca atgcaactaa    6240
taaagccacg tataaaccaa atacctggtg tatacgttgt ctttggagca caaaaccagt    6300
tgaaacatca aattcgtttg atgtactgaa gtcagaggac gcgcagggaa tggataatct    6360
tgcctgcgaa gatctaaaac cagtctctga agaagtagtg gaaaatccta ccatacagaa    6420
agacgttctt gagtgtaatg tgaaaactac cgaagttgta ggagacatta tacttaaacc    6480
agcaaataat agtttaaaaa ttacagaaga ggttggccac acagatctaa tggctgctta    6540
tgtagacaat tctagtctta ctattaagaa acctaatgaa ttatctagag tattaggttt    6600
gaaaaccctt gctactcatg gtttagctgc tgttaatagt gtcccttggg atactatagc    6660
taattatgct aagcctttc ttaacaaagt tgttagtaca actactaaca tagttacacg    6720
gtgtttaaac cgtgtttgta ctaattatat gccttatttc tttactttat tgctacaatt    6780
gtgtactttt actagaagta caaattctag aattaaagca tctatgccga ctactatagc    6840
aaagaatact gttaagagtg tcagtaaatt ttgtctagag gcttcattta attatttgaa    6900 gtcacctaat тттттстaaac tgataaatat tataatttgg tttttactat taagtgttt    6960 cctaggttct ttaatctact caaccgctgc tttaggtgtt ttaatgtcta atttaggcat    7020
gccttcttac tgtactggtt acagagaagg ctatttgaac tctactaatg tcactattgc    7080
aacctactgt actggttcta taccttgtag tgtttgtctt agtggtttag attctttaga    7140
cacctatcct tctttagaaa ctatacaaat taccatttca tcttttaaat gggatttaac    7200
tgcttttggc ttagttgcag agtggttttt ggcatatatt cтттттcacтa ggtttttcta    7260 tgtacttgga ttggctgcaa tcatgcaatt gtttttcagc татттттgcag tacatttt at    7320

tagtaattct tggcttatgt ggttaataat taatcttgta caaatggccc tgatttcagc    7380

tatggttaga atgtacatct tctttgcatc attttatt at gtatggaaaa gttat gtgca    7440

tgttgtagac ggttgtaatt catcaacttg tatgatgtgt tacaaacgta atagagcaac    7500
aagagtcgaa tgtacaacta ttgttaatgg tgttagaagg тcстттттатg tctatgctaa    7560

tggaggtaaa ggcтттттgcа aactacacaa ttggaatt gt gттаатт gt g атacатт cтg    7620
```

```
tgctggtagt acatttatta gtgatgaagt tgcgagagac ttgtcactac agtttaaaag    7680
accaataaat cctactgacc agtcttctta catcgttgat agtgttacag tgaagaatgg    7740
ttccatccat ctttactttg ataaagctgg tcaaaagact tatgaaagac attctctctc    7800
tcattttgtt aacttagaca acctgagagc taataacact aaaggttcat tgcctattaa    7860
tgttatagtt tttgatggta aatcaaaatg tgaagaatca tctgcaaaat cagcgtctgt    7920
ttactacagt cagcttatgt gtcaacctat actgttacta gatcaggcat tagtgtctga    7980
tgttggtgat agtgcggaag ttgcagttaa aatgtttgat gcttacgtta atacgttttc    8040
atcaactttt aacgtaccaa tggaaaaact caaaacacta gttgcaactg cagaagctga    8100
acttgcaaag aatgtgtcct tagacaatgt cttatctact tttatttcag cagctcggca    8160
agggtttgtt gattcagatg tagaaactaa agatgttgtt gaatgtctta aattgtcaca    8220
tcaatctgac atagaagtta ctggcgatag ttgtaataac tatatgctca cctataacaa    8280
agttgaaaac atgacacccc gtgaccttgg tgcttgtatt gactgtagtg cgcgtcatat    8340
taatgcgcag gtagcaaaaa gtcacaacat tgctttgata tggaacgtta aagatttcat    8400
gtcattgtct gaacaactac gaaaacaaat acgtagtgct gctaaaaaga taacttacc    8460
ttttaagttg acatgtgcaa ctactagaca agttgttaat gttgtaacaa caagatagc    8520
acttaagggt ggtaaaattg ttaataattg gttgaagcag ttaattaaag ttacacttgt    8580
gttcctttt gttgctgcta ttttctattt aataacaccct gttcatgtca tgtctaaaca    8640
tactgacttt tcaagtgaaa tcataggata caaggctatt gatggtggtg tcactcgtga    8700
catagcatct acagatactt gttttgctaa caaacatgct gattttgaca catggtttag    8760
ccagcgtggt ggtagttata ctaatgacaa agcttgccca ttgattgctg cagtcataac    8820
aagagaagtg ggttttgtcg tgcctggttt gcctggcacg atattacgca caactaatgg    8880
tgacttttg catttcttac ctagagtttt tagtgcagtt ggtaacatct gttacacacc    8940
atcaaaactt atagagtaca ctgactttgc aacatcagct tgtgttttgg ctgctgaatg    9000
tacaattttt aaagatgctt ctggtaagcc agtaccatat tgttatgata ccaatgtact    9060
agaaggttct gttgcttatg aaagtttacg ccctgacaca cgttatgtgc tcatggatgg    9120
ctctattatt caatttccta acacctacct tgaaggttct gttagagtgg taacaacttt    9180
tgattctgag tactgtaggc acggcacttg tgaaagatca gaagctggtg tttgtgtatc    9240
tactagtggt agatgggtac ttaacaatga ttattacaga tctttaccag gagttttctg    9300
tggtgtagat gctgtaaatt tacttactaa tatgtttaca ccactaattc aacctattgg    9360
tgctttggac atatcagcat ctatagtagc tggtggtatt gtagctatcg tagtaacatg    9420
ccttgcctac tattttatga ggtttagaag agcttttggt gaatacagtc atgtagttgc    9480
ctttaatact ttactattcc ttatgtcatt cactgtactc tgtttaacac cagtttactc    9540
attcttacct ggtgtttatt ctgttatta cttgtacttg acattttatc ttactaatga    9600
tgtttctttt ttagcacata ttcagtggat ggttatgttc acacctttag tacctttctg    9660
gataacaatt gcttatatca tttgtattc cacaaagcat ttctattggt tctttagtaa    9720
ttacctaaag agacgtgtag tctttaatgg tgtttccttt agtactttg aagaagctgc    9780
gctgtgcacc tttttgttaa ataaagaaat gtatctaaag ttgcgtagtg atgtgctatt    9840
acctcttacg caatataata gatacttagc tctttataat aagtacaagt attttagtgg    9900
agcaatggat acaactagct acagagaagc tgcttgttgt catctcgcaa aggctctcaa    9960
tgacttcagt aactcaggtt ctgatgttct ttaccaacca ccacaaacct ctatcacctc    10020
```

```
agctgttttg cagagtggtt ttagaaaaat ggcattccca tctggtaaag ttgagggttg    10080
tatggtacaa gtaacttgtg gtacaactac acttaacggt ctttggcttg atgacgtagt    10140
ttactgtcca agacatgtga tctgcacctc tgaagacatg cttaaccctc attatgaaga    10200
tttactcatt cgtaagtcta atcataattt cttggtacag gctggtaatg ttcaactcag    10260
ggttattgga cattctatgc aaaattgtgt acttaagctt aaggttgata cagccaatcc    10320
taagacacct aagtataagt tgttcgcat tcaaccagga cagactttt cagtgttagc    10380 ttgttacaat ggttcaccat ctggtgttta ccaatgtgct atgaggccca atttcactat    10440
taagggttca ttccttaatg gttcatgtgg tagtgttggt tttaacatag attatgactg    10500
tgtctctttt tgttacatgc accatatgga attaccaact ggagttcatg ctggcacaga    10560
cttagaaggt aacttttatg gaccttttgt tgacaggcaa acagcacaag cagctggtac    10620
ggacacaact attacagtta atgttttagc ttggttgtac gctgctgtta taaatggaga    10680
caggtggttt ctcaatcgat ttaccacaac tcttaatgac tttaaccttg tggctatgaa    10740
gtacaattat gaacctctaa cacaagacca tgttgacata ctaggacctc tttctgctca    10800
aactggaatt gccgttttag atatgtgtgc ttcattaaaa gaattactgc aaaatggtat    10860
gaatggacgt accatattgg gtagtgcttt attagaagat gaatttacac cttttgatgt    10920
tgttagacaa tgctcaggtg ttactttcca aagtgcagtg aaaagaacaa tcaagggtac    10980
acaccactgg ttgttactca caattttgac ttcactttta gttttagtcc agagtactca    11040
atggtctttg ttcttttttt tgtatgaaaa tgccttttta cctttgcta tgggtattat    11100 tgctatgtct gcttttgcaa tgatgtttgt caaacataag catgcatttc tctgttgtt    11160 tttgttacct tctcttgcca ctgtagctta ttttaatatg gtctatatgc ctgctagttg    11220
ggtgatgcgt attatgacat ggttggatat ggttgatact agtttgtctg gttttaagct    11280
aaaagactgt gttatgtatg catcagctgt agtgttacta atccttatga cagcaagaac    11340
tgtgtatgat gatggtgcta ggagagtgtg gacacttatg aatgtcttga cactcgttta    11400
taaagtttat tatggtaatg ctttagatca agccatttcc atgtgggctc ttataatctc    11460
tgttacttct aactactcag gtgtagttac aactgtcatg tttttggcca gaggtattgt    11520
ttttatgtgt gttgagtatt gccctatttt cttcataact ggtaatacac ttcagtgtat    11580
aatgctagtt tattgtttct taggctattt ttgtacttgt actttggcc tcttttgttt    11640 actcaaccgc tactttagac tgactcttgg tgtttatgat tacttagttt ctacacagga    11700
gtttagatat atgaattcac agggactact cccacccaag aatagcatag atgccttcaa    11760
actcaacatt aaattgttgg gtgttggtgg caaaccttgt atcaaagtag ccactgtaca    11820
gtctaaaatg tcagatgtaa agtgcacatc agtagtctta ctctcagttt tgcaacaact    11880
cagagtagaa tcatcatcta aattgtgggc tcaatgtgtc cagttacaca atgacattct    11940
cttagctaaa gatactactg aagccttga aaaaatggtt tcactacttt ctgttttgct    12000
ttccatgcag ggtgctgtag acataaacaa gctttgtgaa gaaatgctgg acaacagggc    12060
aaccttacaa gctatagcct cagagtttag ttcccttcca tcatatgcag cttttgctac    12120
tgctcaagaa gcttatgagc aggctgttgc taatggtgat tctgaagttg ttcttaaaaa    12180
gttgaagaag tctttgaatg tggctaaatc tgaatttgac cgtgatgcag ccatgcaacg    12240
taagttggaa aagatggctg atcaagctat gacccaaatg tataaacagg ctagatctga    12300
ggacaagagg gcaaaagtta ctagtgctat gcagacaatg ctttttcacta tgcttagaaa    12360
```

```
gttggataat gatgcactca acaacattat caacaatgca agagatggtt gtgttccctt    12420
gaacataata cctcttacaa cagcagccaa actaatggtt gtcataccag actataacac    12480
atataaaaat acgtgtgatg gtacaacatt tacttatgca tcagcattgt gggaaatcca    12540
acaggttgta gatgcagata gtaaaattgt tcaacttagt gaaattagta tggacaattc    12600
acctaatttta gcatggcctc ttattgtaac agctttaagg gccaattctg ctgtcaaatt    12660
acagaataat gagcttagtc ctgttgcact acgacagatg tcttgtgctg ccggtactac    12720
acaaactgct tgcactgatg acaatgcgtt agcttactac aacacaacaa agggaggtag    12780
gtttgtactt gcactgttat ccgatttaca ggatttgaaa tgggctagat tccctaagag    12840
tgatggaact ggtactatct atacagaact ggaaccacct tgtaggtttg ttacagacac    12900
acctaaaggt cctaaagtga agtatttata ctttattaaa ggattaaaca acctaaatag    12960
aggtatggta cttggtagtt tagctgccac agtacgtcta caagctggta atgcaacaga    13020
agtgcctgcc aattcaactg tattatcttt ctgtgctttt gctgtagatg ctgctaaagc    13080
ttacaaagat tatctagcta gtgggggaca accaatcact aattgtgtta agatgttgtg    13140
tacacacact ggtactggtc aggcaataac agttacaccg gaagccaata tggatcaaga    13200
atcctttggt ggtgcatcgt gttgtctgta ctgccgttgc cacatagatc atccaaatcc    13260
taaaggattt tgtgacttaa aaggtaagta tgtacaaata cctacaactt gtgctaatga    13320
ccctgtgggt tttacactta aaaacacagt ctgtaccgtc tgcggtatgt ggaaaggtta    13380
tggctgtagt tgtgatcaac tccgcgaacc catgcttcag tcagctgatg cacaatcgtt    13440
tttaaacggg tttgcggtgt aagtgcagcc cgtcttacac cgtgcggcac aggcactagt    13500
actgatgtcg tatacagggc ttttgacatc tacaatgata agtagctgg ttttgctaaa    13560
ttcctaaaaa ctaattgttg tcgcttccaa gaaaaggacg aagatgacaa tttaattgat    13620
tcttactttg tagttaagag acacactttc tctaactacc aacatgaaga aacaatttat    13680
aatttactta aggattgtcc agctgttgct aaacatgact tctttaagtt tagaatagac    13740
ggtgacatgg taccacatat atcacgtcaa cgtcttacta aatacacaat ggcagacctc    13800
gtctatgctt taaggcattt tgatgaaggt aattgtgaca cattaaaaga aatacttgtc    13860
acatacaatt gttgtgatga tgattatttc aataaaaagg actggtatga ttttgtagaa    13920
aacccagata tattacgcgt atacgccaac ttaggtgaac gtgtacgcca agcttttgtta    13980
aaaacagtac aattctgtga tgccatgcga aatgctggta ttgttggtgt actgacatta    14040
gataatcaag atctcaatgg taactggtat gatttcggtg atttcataca aaccacgcca    14100
ggtagtggag ttcctgttgt agattcttat tattcattgt taatgcctat attaaccttg    14160
accagggctt taactgcaga gtcacatgtt gacactgact taacaaagcc ttacattaag    14220
tgggatttgt taaatatga cttcacggaa gagaggttaa aactctttga ccgttatttt    14280
aaatattggg atcagacata ccacccaaat tgtgttaact gtttggatga cagatgcatt    14340
ctgcattgtg caaactttaa tgtttttattc tctacagtgt tcccacctac aagttttgga    14400
ccactagtga gaaaaatatt tgttgatggt gttccatttg tagtttcaac tggataccac    14460
ttcagagagc taggtgttgt acataatcag gatgtaaact acatagctc tagacttagt    14520
tttaaggaat tacttgtgta tgctgctgac cctgctatgc acgctgcttc tggtaatcta    14580
ttactagata aacgcactac gtgcttttca gtagctgcac ttactaacaa tgttgctttt    14640
caaactgtca aacccggtaa ttttaacaaa gacttctatg actttgctgt gtctaagggt    14700
ttctttaagg aaggaagttc tgttgaatta aaacacttct tctttgctca ggatggtaat    14760
```

```
gctgctatca gcgattatga ctactatcgt tataatctac caacaatgtg tgatatcaga   14820
caactactat ttgtagttga agttgttgat aagtactttg attgttacga tggtggctgt   14880
attaatgcta accaagtcat cgtcaacaac ctagacaaat cagctggttt tccatttaat   14940
aaatggggta aggctagact ttattatgat tcaatgagtt atgaggatca agatgcactt   15000
ttcgcatata caaaacgtaa tgtcatccct actataactc aaatgaatct aagtatgcc    15060 attagtgcaa agaatagagc tcgcaccgta gctggtgtct ctatctgtag tactatgacc   15120
aatagacagt ttcatcaaaa attattgaaa tcaatagccg ccactagagg agctactgta   15180
gtaattggaa caagcaaatt ctatggtggt tggcacaaca tgttaaaaac tgtttatagt   15240
gatgtagaaa accctcacct tatgggttgg gattatccta aatgtgatag agccatgcct   15300
aacatgctta gaattatggc ctcacttgtt cttgctcgca acatacaac gtgttgtagc    15360 ttgtcacacc gtttctatag attagctaat gagtgtgctc aagtattgag tgaaatggtc   15420
atgtgtggcg ttcactata tgttaaacca ggtggaacct catcaggaga tgccacaact    15480
gcttatgcta atagtgtttt taacatttgt caagctgtca cggccaatgt taatgcactt   15540
ttatctactg atggtaacaa aattgccgat aagtatgtcc gcaatttaca acacagactt   15600
tatgagtgtc tctatagaaa tagagatgtt gacacagact ttgtgaatga ttttacgca    15660 tatttgcgta acatttctc aatgatgata ctctctgacg atgctgttgt gtgtttcaat   15720
agcacttatg catctcaagg tctagtggct agcataaaga actttaagtc agttctttat   15780
tatcaaaaca atgtttttat gtctgaagca aaatgttgga ctgagactga ccttactaaa   15840
ggacctcatg aattttgctc tcaacataca atgctagtta acagggtga tgattatgtg    15900 taccttcctt acccagatcc atcaagaatc ctaggggccg gctgttttgt agatgatatc   15960
gtaaaaacag atggtacact tatgattgaa cggttcgtgt ctttagctat agatgcttac   16020
ccacttacta aacatcctaa tcaggagtat gctgatgtct ttcatttgta cttacaatac   16080
ataagaaagc tacatgatga gttaacagga cacatgttag acatgtattc tgttatgctt   16140
actaatgata acacttcaag gtattgggaa cctgagttt atgaggctat gtacacaccg    16200
catacagtct tacaggctgt tggggcttgt gttctttgca attcacagac ttcattaaga   16260
tgtggtgctt gcatacgtag accattctta tgttgtaaat gctgttacga ccatgtcata   16320
tcaacatcac ataaattagt cttgtctgtt aatccgtatg tttgcaatgc tccaggttgt   16380
gatgtcacag atgtgactca actttactta ggaggtatga gctattattg taaatcacat   16440
aaaccaccca ttagttttcc attgtgtgct aatggacaag ttttggttt atataaaaat    16500 acatgtgttg gtagcgataa tgttactgac tttaatgcaa ttgcaacatg tgactggaca   16560
aatgctggta attacatttt agctaacacc tgtactgaaa gactcaagct ttttgcagca   16620
gaaacgctca agctactga ggagacattt aaactgtctt atggtattgc tactgtacgt   16680
gaagtgctgt ctgacagaga attacatctt tcatgggaag ttggtaaacc tagaccacca   16740
cttaaccgaa attatgtctt tactggttat cgtgtaacta aaaacagtaa agtacaaata   16800
ggagagtaca cctttgaaaa aggtgactat ggtgatgctg ttgtttaccg aggtacaaca   16860
acttacaaat taaatgttgg tgattatttt gtgctgacat cacatacagt aatgccatta   16920
agtgcaccta cactagtgcc acaagagcac tatgttagaa ttactggctt ataccaaaca    16980
ctcaatatct cagatgagtt ttctagcaat gttgcaaatt atcaaaaggt tggtatgcaa    17040
aagtattcta cactccaggg accacctggt actggtaaga gtcatttttgc tattggccta   17100
```

```
gctctctact acccttctgc tcgcatagtg tatacagctt gctctcatgc cgctgttgat    17160
gcactatgtg agaaggcatt aaaatatttg cctatagata aatgtagtag aattatacct    17220
gcacgtgctc gtgtagagtg ttttgataaa ttcaaagtga attcaacatt agaacagtat    17280
gtcttttgta ctgtaaatgc attgcctgag acgacagcag atatagttgt ctttgatgaa    17340
atttcaatgg ccacaaatta tgatttgagt gttgtcaatg ccagattacg tgctaagcac    17400
tatgtgtaca ttagcgaccc tgctcaatta cctgcaccac gcacattgct aactaagggc    17460
acactagaac cagaatattt caattcagtg tgtagactta tgaaaactat aggtccagac    17520
atgttcctcg gaacttgtcg gcgttgtcct gctgaaattg ttgacactgt gagtgctttg    17580
gtttatgata ataagcttaa agcacataaa gacaaatcag ctcaatgctt taaaatgttt    17640
tataagggtg ttatcacgca tgatgttttca tctgcaatta acaggccaca aataggcgtg    17700
gtaagagaat tccttacacg taaccctgct tggagaaaag ctgtctttat ttcacccttat    17760 aattcacaga atgctgtagc ctcaaagatt ttgggactac caactcaaac tgttgattca    17820
tcacagggct cagaatatga ctatgtcata ttcactcaaa ccactgaaac agctcactct    17880
tgtaatgtaa acagatttaa tgttgctatt accagagcaa agtaggcat actttgcata    17940 atgtctgata gagaccttta tgacaagttg caatttacaa gtcttgaaat tccacgtagg    18000
aatgtggcaa ctttacaagc tgaaaatgta acaggactct ttaaagattg tagtaaggta    18060
atcactgggt tacatcctac acaggcacct acacacctca gtgttgacac taaattcaaa    18120
actgaaggtt tatgtgttga catacctggc ataccttaagg acatgaccta tagaagactc    18180
atctctatga tgggttttaa aatgaattat caagttaatg gttaccctaa catgtttatc    18240
acccgcgaag aagctataag acatgtacgt gcatggattg gcttcgatgt cgagggggtgt    18300 catgctacta gagaagctgt tggtaccaat ttacctttac agctaggttt ttctacaggt    18360
gttaacctag ttgctgtacc tacaggttat gttgatacac ctaataatac agattttttcc    18420 agagttagtg ctaaaccacc gcctggagat caatttaaac accttatacc acttatgtac    18480
aaaggacttc cttggaatgt agtgcgtata aagattgtac aaatgttaag tgacacactt    18540
aaaaatctct ctgacagagt cgtatttgtc ttatgggcac atggctttga gttgacatct    18600
atgaagtatt ttgtgaaaat aggacctgag cgcacctgtt gtctatgtga tagacgtgcc    18660
acatgctttt ccactgcttc agacacttat gcctgttggc atcattctat ggatttgat    18720 tacgtctata atccgtttat gattgatgtt caacaatggg gtttttacagg taacctacaa    18780 agcaaccatg atctgtattg tcaagtccat ggtaatgcac atgtagctag ttgtgatgca    18840
atcatgacta ggtgtctagc tgtccacgag tgctttgtta agcgtgttga ctggactatt    18900
gaatatccta taattggtga tgaactgaag attaatgcgg cttgtagaaa ggttcaacac    18960
atggttgtta agctgcatt attagcagac aaattcccag ttcttcacga cattggtaac    19020
cctaaagcta ttaagtgtgt acctcaagct gatgtagaat ggaagttcta tgatgcacag    19080
ccttgtagtg acaaagctta taaaatagaa gaattattct attcttatgc cacacattct    19140
gacaaattca cagatggtgt atgcctattt tggaattgca atgtcgatag atatcctgct    19200
aattccattg tttgtagatt tgacactaga gtgctatcta accttaactt gcctggttgt    19260
gatggtggca gtttgtatgt aaataaacat gcattccaca caccagcttt tgataaaagt    19320
gcttttgtta atttaaaaca attaccattt ttctattact ctgacagtcc atgtgagtct    19380
catggaaaac aagtagtgtc agatatagat tatgtaccac taaagtctgc tacgtgtata    19440
acacgttgca atttaggtgg tgctgtctgt agacatcatg ctaatgagta cagattgtat    19500
```

```
ctcgatgctt ataacatgat gatctcagct ggctttagct tgtgggttta caaacaattt   19560
gatacttata acctctggaa cacttttaca agacttcaga gtttagaaaa tgtggctttt   19620
aatgttgtaa ataagggaca ctttgatgga caacagggtg aagtaccagt ttctatcatt   19680
aataacactg tttacacaaa agttgatggt gttgatgtag aattgtttga aaataaaaca   19740
acattacctg ttaatgtagc atttgagctt tgggctaagc gcaacattaa accagtacca   19800
gaggtgaaaa tactcaataa tttgggtgtg gacattgctg ctaatactgt gatctgggac   19860
tacaaaagag atgctccagc acatatatct actattggtg tttgttctat gactgacata   19920
gccaagaaac caactgaaac gatttgtgca ccactcactg tcttttttga tggtagagtt   19980
gatggtcaag tagacttatt tagaaatgcc cgtaatggtg ttcttattac agaaggtagt   20040
gttaaaggtt tacaaccatc tgtaggtccc aaacaagcta gtcttaatgg agtcacatta   20100
attggagaag ccgtaaaaac acagttcaat tattataaga agttgatgg tgttgtccag   20160 caattacctg aaacttactt tactcagagt agaaatttac aagaatttaa acccaggagt   20220
caaatggaaa ttgatttctt agaattagct atggatgaat tcattgaacg gtataaatta   20280
gaaggctatg ccttcgaaca tatcatttat ggagatttta gtcatagtca gttaggtggt   20340
ttacatctac tgattggact agctaaacgt tttaaggaat caccttttga attagaagat   20400
tttattccta tggacagtac agttaaaaac tatttcataa cagatgcgca acaggttca   20460 tctaagtgtg tgtgttctgt tattgattta ttacttgatg attttgttga aataataaaa   20520
tcccaagatt tatctgtagt ttctaaggtt gtcaaagtga ctattgacta tacagaaatt   20580
tcatttatgc tttggtgtaa agatggccat gtagaaacat tttacccaaa attacaatct   20640
agtcaagcat ggcaaccagg tgttgctatg cctaatcttt acaaaatgca agaatgctta   20700
ttagaaaagt gtgaccttca aaattatggt gatagtgcaa cattacctaa aggcataatg   20760
atgaatgtcg caaaatatac tcaactgtgt caatatttaa acacattaac attagctgta   20820
ccctataata tgagagttat acattttggt gctggttctg ataaaggagt tgcaccaggt   20880
acagctgttt taagacagtg gttgcctacg ggtacgctgc ttgtcgattc agatcttaat   20940
gactttgtct ctgatgcaga ttcaactttg attggtgatt gtgcaactgt acatacagct   21000
aataaatggg atctcattat tagtgatatg tacgacccta agactaaaaa tgttacaaaa   21060
gaaaatgact ctaagagggg tttttcact tacatttgtg ggtttataca acaaagcta   21120 gctcttggag gttccgtggc tataaagata acagaacatt cttggaatgc tgatctttat   21180
aagctcatgg gacacttcgc atggtggaca gcctttgtta ctaatgtgaa tgcgtcatca   21240
tctgaagcat tttaattgg atgtaattat cttggcaaac cacgcgaaca aatagatggt   21300
tacgtaatgc atgcaaatta catttttgg aggaatacaa atccaattca gttgtcttcc   21360
tattctttat ttgacatgag taaatttccc cttaaattaa ggggtactgc tgttatgtct   21420 ttaaagaag gtcaaatcaa tgatatgatt ttatctcttc ttagtaaagg tagacttata   21480
attagagaaa acaacagagt tgttatttct agtgatgttc ttgttaacaa ctaaacgaac   21540
aatgtttgtt tttcttgttt tattgccact agtctctagt cagtgtgtta atcttacaac   21600
cagaactcaa ttaccccctg catacactaa ttctttcaca cgtggtgttt attaccctga   21660
caaagttttc agatcctcag ttttacattc aactcaggac ttgttcttac ctttctttc   21720 caatgttact ggttccatg ctatacagt ctctgggacc aatggtacta agaggtttga   21780
taaccctgtc ctaccattta atgatggtgt ttattttgct tccactgaga agtctaacat   21840
```

```
aataagaggc tggatttttg gtactacttt agattcgaag acccagtccc tacttattgt   21900
taataacgct actaatgttg ttattaaagt ctgtgaattt caattttgta atgatccatt   21960
tttgggtgtt tattaccaca aaaacaacaa aagttggatg gaaagtgagt tcagagttta   22020
ttctagtgcg aataattgca cttttgaata tgtctctcag ccttttctta tggaccttga   22080
aggaaaacag ggtaatttca aaaatcttag ggaatttgtg tttaagaata ttgatggtta   22140 tttaaaata tattctaagc acacgcctat taatttagtg cgtgatctcc ctcaggggtt   22200
ttcggcttta gaaccattgg tagatttgcc aataggtatt aacatcacta ggtttcaaac   22260
tttacttgct ttacatagaa gttatttgac tcctggtgat tcttcttcag gttggacagc   22320
tggtgctgca gcttattatg tgggttatct tcaacctagg acttttctat taaaatataa   22380
tgaaaatgga accattacag ttgctgtagc ctgtgcactt gaccctctct cagaaacaaa   22440
gtgtacgttg aaatccttca ctgtagaaaa aggaatctat caaacttcta actttagagt   22500
ccaaccaaca gaatctattg ttagatttcc taatattaca aacttgtgcc cttttggtga   22560
agtttttaac gccaccagat ttgcatctgt ttatgcttgg aacaggaaga gaatcagcaa   22620
ctgtgttgct gattattctg tcctatataa ttccgcatca ttttccactt ttaagtgtta   22680
tggagtgtct cctactaaat taaatgatct ctgctttact aatgtctatg cagattcatt   22740
tgtaattaga ggtgatgaag tcagacaaat cgctccaggg caaactggaa agattgctga   22800
ttataattat aaattaccag atgatttac aggctgcgtt atagcttgga attctaacaa   22860
tcttgattct aaggttggtg gtaattataa ttacctgtat agattgttta ggaagtctaa   22920
tctcaaacct tttgagagag atatttcaac tgaaatctat caggccggta gcacaccttg   22980
taatggtgtt gaaggtttta attgttactt tcctttacaa tcatatggtt tccaacccac   23040
taatggtgtt ggttaccaac catacagagt agtagtactt tcttttgaac ttctacatgc   23100
accagcaact gtttgtggac ctaaaaagtc tactaatttg gttaaaaaca atgtgtcaa   23160 tttcaacttc aatggtttaa caggcacagg tgttcttact gagtctaaca aaaagtttct   23220
gcctttccaa caatttggca gagacattgc tgacactact gatgctgtcc gtgatccaca   23280
gacacttgag attcttgaca ttacaccatg ttctttggt ggtgtcagtg ttataacacc   23340
aggagcaaat acatctaacc aagttactgt tctttatcag gatgttaact gcacagaagt   23400
ccctgttgct attcatgcag atcaacttac tcctacttgg cgtgtttatt ctacaggttc   23460
taatgttttc aaaacacgtg caggctgttt aataggggct gaacatgtca caactcata   23520 tgagtgtgac atacccattg gtgcaggtat atgcgctagt tatcaaactc agactaattc   23580
tcctcggcgg gcacgaagta cagctagtca atccatcatt gcctacacta tgtcacttgg   23640
tgcagaaaat tcagttgctt actctaacaa ctctattgtc atacccacaa attttactat   23700
tagtgttacc acagaaattc taccagtgtc tatgaccaag acatcagtag attgtacaat   23760
gtacatttgt agtgattcaa ctgaatgcag caatccttg ttacaatatg gcagttttg   23820 cacacaatta aaccgtgctt taactggaat agctgttgaa caagacaaaa acacccaaga   23880 agttttgca caagtcaaac aaatttacaa acaccacca attaaagatt tggtggttt   23940 taatttttca caaatattac cagatccatc aaaaccaagc aagaggtcat ttattgaaga   24000
tctacttttc aacaaagtga cacttgcaga tgctggcttc atcaaacaat atggtgattg   24060
ccttggtgat attgctgcta gagacctcat ttgtgcacaa aagtttaacg gccttactgt   24120
tttgccacct ttgctcacag atgaaatgat tgctcaatac acttctgcac tgttagcggg   24180
tacaatcact tctggttgga cctttggtgc aggtgctgca ttacaaatac catttgctat   24240
```

```
gcaaatggct tataggttta atggtattag agttacacag aatgttctct atgagaacca    24300
aaaattgatt gccaaccaat ttaatagtgc tattggcaaa attcaagact cactttcttc    24360
cacagcaagt gcacttggaa aacttcaaga tgtggtcaac caaaatgcac aagctttaaa    24420
cacgcttgtt aaacaactta gctccacttt cagcacaatt tcaagtgttt taaatgatat    24480
cctttcacgt cttgacaaag ttgaggctga agtgcaaatt gataggttga tcacaggcag    24540
acttcaaagt ttgcagacat atgtgactca acaattaatt agagctgcag aaatcagagc    24600
ttctgctaat cttaaggcta ctaaaatgtc agagtgtgta cttggacaat caaaaagagt    24660 tgattttgt ggaaagggct atcatcttat gtccttccct cagtcagcac ctcatggtgt    24720
agtcttcttg catgtgactt atgtccctgc acaagaaaag aacttcacaa ctgctcctgc    24780
cacttgtcat gatggaaaag cacactttcc tcgtgaaggt gtctttgttt caaatggcac    24840
acactggttt gtaacacaaa ggaattttga tgaaccacaa atcattacta cagacaacac    24900
atttgtgtct ggtaactgtg atgttgtaat aggaattgtc aacaacacag tttatgatcc    24960
tttgcaacct gaattagact cattcaagga ggagttagat aaatatttta agaatcatac    25020
atcaccagat gttgatttag gtgacatctc tggcattaat gcttcagttg taaacattca    25080
aaaagaaatt gaccgcctca atgaggttgc caagaattta aatgaatctc tcatcgatct    25140
ccaagaactt ggaaagtatg agcagtatat aaaatggcca tggtacattt ggctaggttt    25200
tatagctggc ttgattgcca tagtaatggt gacaattatg ctttgctgta tgaccagttg    25260
ctgtagttgt ctcaagggct gttgttcttg tggatcctgc tgcaaatttg atgaagacga    25320
ctctgagcca gtgctcaaag gagtcaaatt acattacaca taaacgaact tatggatttg    25380
tttatgagaa tcttcacaat tggaactgta actttgaagc aaggtgaaat caaggatgct    25440
actccttcag attttgttcg cgctactgca acgataccga tacaagcctc actccctttc    25500
ggatggctta ttgttggcgt tgcacttctt gctgtttttc agagcgcttc caaaatcata    25560
accctcaaaa agagatggca actagcactc tccaagggtg ttcactttgt ttgcaacttg    25620
ctgttgttgt ttgtaacagt ttactcacac cttttgctcg ttgctgctgg cttgtaagcc    25680
ccttttctct atctttatgc tttagtctac ttcttgcaga gtataaactt tgtaagaata    25740
ataatgaggc tttggctttg ctggaaatgc cgttccaaaa acccattact ttatgatgcc    25800
aactattttc tttgctggca tactaattgt tatgactatt gtatacctta caatagtgta    25860
acttcttcaa ttgtcattac ttcaggtgat ggcacaacaa gtcctatttc tgaacatgac    25920
taccagattg gtggttatac tgaaaaatgg gaatctggag taaaagactg tgttgtatta    25980
cacagttact tcacttcaga ctattaccag ctgtactcaa ctcaattgag tacagacact    26040
ggtgttgaac atgttacctt cttcatctac aataaaattg ttgatgagcc tgaagaacat    26100
gtccaaattc acacaatcga cggttcatcc ggagttgtta atccagtaat ggaaccaatt    26160
tatgatgaac cgacgacgac tactagcgtg ccttttgtaat gcacaagctg atgagtacga    26220
acttatgtac tcattcgttt cggaagagac aggtacgtta atagttaata gcgtacttct    26280
ttttcttgct ttcgtggtat tcttgctagt tacactagcc atccttactg cgcttcgatt    26340
gtgtgcgtac tgctgcaata ttgttaacgt gagtcttgta aaaccttctt tttacgttta    26400
ctctcgtgtt aaaaatctga attcttctag agttcctgat cttctggtct aaacgaacta    26460
aatattatat tagttttttct gtttggaact ttaattttag ccatggcaga ttccaacggt    26520
actattaccg ttgaagagct taaaaagctc cttgaacaat ggaacctagt aataggtttc    26580
```

```
ctattccttt catggatttg tcttctacaa tttgcctatg ccaacaggaa taggttttg      26640
tatataatta agttaatttt cctctggctg ttatggccag taactttagc ttgttttgtg    26700
cttgctgctg tttacagaat aaattggatc accggtggaa ttgctatcgc aatggcttgt    26760
cttgtaggct tgatgtggct cagctacttc attgcttctt tcagactgtt tgcgcgtacg    26820
cgttccatgt ggtcattcaa tccagaaact aacattcttc tcaacgtgcc actccatggc    26880
actattctga ccagaccgct tctagaaagt gaactcgtaa tcggagctgt gatccttcgt    26940
ggacatcttc gtattgctgg acaccatcta ggacgctgtg acatcaagga cctgcctaaa    27000
gaaatcactg ttgctacatc acgaacgctt tcttattaca aattgggagc ttcgcagcgt    27060
gtagcaggtg actcaggttt tgctgcatac agtcgctaca ggattggcaa ctataaatta    27120
aacacagacc attccagtag cagtgacaat attgctttgc ttgtacagta agtgacaaca    27180
gatgtttcat ctcgttgact ttcaggttac tatagcagag atattactaa ttattatgag    27240
gacttttaaa gtttccattt ggaatcttga ttacatcata aacctcataa ttaaaaattt    27300
atctaagtca ctaactgaga ataaatattc tcaattagat gaagagcaac caatggagat    27360
tgattaaacg aacatgaaaa ttattctttt cttggcactg ataacactcg ctacttgtga    27420
gctttatcac taccaagagt gtgttagagg tacaacagta cttttaaaag aaccttgctc    27480
ttctggaaca tacgagggca attcaccatt tcatcctcta gctgataaca aatttgcact    27540
gacttgcttt agcactcaat ttgcttttgc ttgtcctgac ggcgtaaaac acgtctatca    27600
gttacgtgcc agatcagttt cacctaaact gttcatcaga caagaggaag ttcaagaact    27660
ttactctcca ttttttctta ttgttgcggc aatagtgttt ataacacttt gcttcacact    27720
caaaagaaag acagaatgat tgaactttca ttaattgact tctatttgtg cttttttagcc   27780
tttctgctat tccttgtttt aattatgctt attatctttt ggttctcact tgaactgcaa    27840
gatcataatg aaacttgtca cgcctaaacg aacatgaaat ttcttgtttt cttaggaatc    27900
atcacaactg tagctgcatt tcaccaagaa tgtagtttac agtcatgtac gcaatatcaa    27960
ccacatgtag ttgatgaccc gtgtcctatt cacttctatt ctaaatggta tattagagta    28020
ggagctagaa aatcagcacc tttaattgaa ttgtgcgtgg atgaggctgg ttctaaatca    28080
cccattcagt acatcgatat cggtaattat acagtttcct gtttaccttt tacaattaat    28140
tgccaggaac ctaaattggg tagtcttgta gtgcgttgtt cgttctatga agacttttta    28200
gagtatcatg acgttcgtgt tgtttagat ttcatctaaa cgaacaaact aaaatgtctg    28260
ataatggacc ccaaaatcag cgaaatgcac cccgcattgc ttttggtgga ccctcagatt    28320
caactggcag taaccagaat ggagaacgca gtggggcgcg atcaaaacaa cgtcggcccc    28380
aaggtttacc caataatact gcgtcttggt tcaccgctct cactcaacat ggcaaggaag    28440
accttaaatt ccctcgagga caaggcgttc aattaacaca caatagcagt ccagatgacc    28500
aaattggcta ctaccgaaga gctaccagac gaattcgtgg tggtgacggt aaaatgaaag    28560
atctcagtcc aagatggtat ttctactacc taggaactgg gccagaagct ggacttccct    28620
atggtgctaa caaagacggc atcatatggg ttgcaactga gggagccttg aatacaccaa    28680
aagatcacat tggcacccgc aatcctgcta acaatgctgc aatcgtgcta caacttcctc    28740
aaggaacaac attgccaaaa ggcttctacg cagaagggag cagaggcggc agtcaagcct    28800
cttctcgttc ctcatcacgt agtcgcaaca gttcaagaaa ttcaactcca ggcagcagta    28860
ggggaacttc tcctgctaga atggctggca atggcggtga tgctgctctt gctttgctgc    28920
tgcttgacag attgaaccag cttgagagca aaatgtctgg taaaggccaa caacaacaag    28980
```

```
gccaaactgt cactaagaaa tctgctgctg aggcttctaa gaagcctcgg caaaaacgta   29040
ctgccactaa agcatacaat gtaacacaag ctttcggcag acgtggtcca gaacaaaccc   29100
aaggaaattt tggggaccag gaactaatca gacaaggaac tgattacaaa cattggccgc   29160
aaattgcaca atttgcccCC agcgcttcag cgttcttcgg aatgtcgcgc attggcatgg   29220
aagtcacacc ttcgggaacg tggttgacct acacaggtgc catcaaattg gatgacaaag   29280
atccaaattt caaagatcaa gtcattttgc tgaataagca tattgacgca tacaaaacat   29340
tcccaccaac agagcctaaa aaggacaaaa agaagaaggc tgatgaaact caagccttac   29400
cgcagagaca gaagaaacag caaactgtga ctcttcttcc tgctgcagat ttggatgatt   29460
tctccaaaca attgcaacaa tccatgagca gtgctgactc aactcaggcc taaactcatg   29520
cagaccacac aaggcagatg ggcaatacaa acgttttcgc ttttccgttt acgatatata   29580
gtctactctt gtgcagaatg aattctcgta actacatagc acaagtagat gtagttaact   29640
ttaatctcac atagcaatct ttaatcagtg tgtaacatta gggaggactt gaaagagcca   29700
ccacattttc accgaggcca cgcggagtac gatcgagtgt acagtgaaca atgctaggga   29760
gagctgccta tatggaagag ccctaatg                                      29788
```